US010679294B1

(12) United States Patent
Lanzrath

(10) Patent No.: US 10,679,294 B1
(45) Date of Patent: Jun. 9, 2020

(54) METHODS FOR ESTIMATING MORTALITY RISK OF AN INDIVIDUAL AMONG A PEER GROUP

(71) Applicant: Quest Diagnostics Investments Incorporated, Wilmington, DE (US)

(72) Inventor: Brian Lanzrath, Olathe, KS (US)

(73) Assignee: QUEST DIAGNOSTICS INVESTMENTS INCORPORATED, Wilmington, DE (US)

( * ) Notice: Subject to any disclaimer, the term of this patent is extended or adjusted under 35 U.S.C. 154(b) by 929 days.

(21) Appl. No.: 14/874,723

(22) Filed: Oct. 5, 2015

Related U.S. Application Data

(63) Continuation of application No. 13/340,541, filed on Dec. 29, 2011, now abandoned.

(60) Provisional application No. 61/428,597, filed on Dec. 30, 2010.

(51) Int. Cl.
*G06Q 40/08* (2012.01)
*G16H 10/40* (2018.01)
*G16H 50/30* (2018.01)

(52) U.S. Cl.
CPC ............ *G06Q 40/08* (2013.01); *G16H 10/40* (2018.01); *G16H 50/30* (2018.01)

(58) Field of Classification Search
CPC ......... G16H 50/30; G16H 10/40; G06Q 40/08
USPC .................................................. 705/2-4
See application file for complete search history.

(56) References Cited

U.S. PATENT DOCUMENTS

2002/0087364 A1* 7/2002 Lerner .................. G06Q 40/08
705/4
2009/0265190 A1* 10/2009 Ashley .................. G06Q 40/08
705/4

FOREIGN PATENT DOCUMENTS

WO  WO-2005048050 A2 *  5/2005  ............. G06Q 40/08

OTHER PUBLICATIONS

Cox, Samuel H., "Mortality Risk Modeling: Applications to Insurance Securitization," 4th International Longevity Risk and Capital Market Solutions Symposium 2008 (Year: 2008).*
"Report of the Society of Actuaries Early Duration Claims Survey Subcommittee," Dec. 2009, 60 pages (accessed at http://66.216.104.121/Research/Experience-Study/Bus-Practice-Surveys/early-duration-claims.aspx).
Dolan, V.F., et al., "Glucosuria as a Mortality Risk Predictor when Blood is Not Collected," On the Risk, vol. 26, No. 2, 2010, pp. 46-51.
ExamOne Risk IQ Launch, "Innovation in Insurance Underwriting: ExamOne Introduces Risk IQ," Sep. 16, 2010, 2 pages.
Fulks, et al., "Using Liver Enzymes as Screening Tests to Predict Mortality Risk," J Insur Med. 2008,40, pp. 191-203.
Lanzrath, B., et al., "A Comprehensive Multivariate Approach to the Stratification of Applicant-Level All-Cause Mortality Risk," On the Risk, vol. 27, No. 1, 2011, pp. 56-61.
Population Reference Bureau, "Use of Biomarkers in Predicting Health and Mortality," Today's Research on Aging, No. 14, Sep. 2008, pp. 1-6.

* cited by examiner

*Primary Examiner* — John P Go
(74) *Attorney, Agent, or Firm* — Foley & Lardner LLP

(57) ABSTRACT

A method for determining the relative mortality risk of an individual as compared to their age/sex/tobacco-use peers. This relative mortality risk may be used in underwriting a life or medical insurance policy.

14 Claims, 19 Drawing Sheets

Figure 2A

| Gender | | Females | | | | | Males | | | | |
|---|---|---|---|---|---|---|---|---|---|---|---|
| Age Range | | 20 | 30 | 40 | 50 | 60 | 20 | 30 | 40 | 50 | 60 |
| BPSYST1 | Min | 88 | 88.15 | 89.71 | 90.36 | 95.2 | 93.78 | 95.58 | 97.53 | 98.52 | 99.72 |
| | Median | 109.61 | 109.88 | 112.61 | 119.61 | 122.75 | 118.61 | 119.46 | 120.25 | 122.34 | 125.53 |
| | Max | 134.93 | 138.65 | 146.13 | 157.73 | 166.58 | 143.78 | 146.41 | 152.12 | 160.24 | 165.77 |
| BPDIAS1 | Min | 53.81 | 55.54 | 58.15 | 61.81 | 61.25 | 56.35 | 58.35 | 59.76 | 59.8 | 59.27 |
| | Median | 73.28 | 74.83 | 76.81 | 80.5 | 81.21 | 73.99 | 76.3 | 78.12 | 78.53 | 78.17 |
| | Max | 94.21 | 96.4 | 100.81 | 104.69 | 104.76 | 92.19 | 96.43 | 99.69 | 100.07 | 99.58 |
| ALB | Min | 3.4 | 3.4 | 3.7 | 3.8 | 3.7 | 4.1 | 4.1 | 4 | 3.9 | 3.8 |
| | Median | 4.5 | 4.4 | 4.4 | 4.5 | 4.4 | 4.8 | 4.7 | 4.6 | 4.6 | 4.5 |
| | Max | 5.2 | 5.1 | 5.1 | 5.1 | 5 | 5.4 | 5.3 | 5.3 | 5.2 | 5.1 |
| ALK_PHOS | Min | 28.13 | 28 | 28.13 | 32.01 | 33.22 | 35.11 | 34 | 33.95 | 33.22 | 33 |
| | Median | 60 | 59 | 59.17 | 71 | 72 | 68.87 | 66 | 66 | 66.93 | 67 |
| | Max | 145.2 | 136 | 128 | 148 | 151 | 129.01 | 124 | 126.1 | 130.01 | 134.83 |
| BILI | Min | 0.2 | 0.2 | 0.2 | 0.2 | 0.2 | 0.3 | 0.3 | 0.3 | 0.3 | 0.3 |
| | Median | 0.5 | 0.5 | 0.5 | 0.5 | 0.5 | 0.7 | 0.7 | 0.7 | 0.7 | 0.7 |
| | Max | 1.6 | 1.6 | 1.5 | 1.5 | 1.5 | 2.3 | 2.1 | 2 | 2 | 2 |
| BUN | Min | 6 | 6 | 7 | 8 | 8 | 8 | 9 | 9 | 9 | 9 |
| | Median | 12 | 13 | 14 | 15 | 17 | 15 | 16 | 16 | 17 | 18 |
| | Max | 22 | 23 | 24 | 28 | 35 | 26 | 26 | 28 | 30 | 35 |
| CHOL | Min | 112 | 117 | 125 | 130 | 125 | 110 | 120 | 124 | 118 | 110 |
| | Median | 176 | 182 | 193 | 207 | 205 | 179 | 196 | 202 | 199 | 187 |
| | Max | 296 | 296 | 294 | 315 | 317 | 284 | 303 | 311 | 307 | 293 |
| CREAT | Min | 0.5 | 0.5 | 0.5 | 0.5 | 0.6 | 0.7 | 0.7 | 0.7 | 0.7 | 0.7 |
| | Median | 0.8 | 0.8 | 0.8 | 0.8 | 0.8 | 1 | 1 | 1 | 1 | 1.1 |
| | Max | 1.2 | 1.2 | 1.2 | 1.3 | 1.6 | 1.5 | 1.5 | 1.6 | 1.6 | 1.9 |
| GGT | Min | 6 | 6 | 7 | 8 | 8 | 9 | 10 | 10 | 11 | 10 |
| | Median | 14 | 14 | 16 | 19 | 20 | 22 | 26 | 28 | 28 | 25 |
| | Max | 34 | 41 | 54 | 74 | 70 | 65 | 82 | 96 | 96 | 81 |

| | | | | | | | | | | | |
|---|---|---|---|---|---|---|---|---|---|---|---|
| GLUC | Min | 60.43 | 60.46 | 60.57 | 60.99 | 61.32 | 60.59 | 60.68 | 61.01 | 61.29 | 61.47 |
| | Median | 79.63 | 81.23 | 83.4 | 85.77 | 88.17 | 83.13 | 84.77 | 86.96 | 88.97 | 90.94 |
| | Max | 125.87 | 136.76 | 167.98 | 217.81 | 226.1 | 134.49 | 159 | 210.11 | 207 | 230.63 |
| AST | Min | 10 | 10 | 10 | 11 | 11 | 11 | 12 | 12 | 12 | 12 |
| | Median | 17 | 17 | 18 | 19.66 | 20 | 21 | 22 | 22 | 22 | 21 |
| | Max | 46 | 47 | 50 | 58 | 55 | 69 | 65 | 65 | 64 | 58 |
| ALT | Min | 5.12 | 5.83 | 5.97 | 6.96 | 6.86 | 7.66 | 8.79 | 9.26 | 9.19 | 8.14 |
| | Median | 13.15 | 13.64 | 14.38 | 17.15 | 16.74 | 21.5 | 24.09 | 24.35 | 23.15 | 20.41 |
| | Max | 33.22 | 33.8 | 35.02 | 41.26 | 36.56 | 61.1 | 62.03 | 57.9 | 51.27 | 42.76 |
| PROT | Min | 6 | 6 | 6.2 | 6.2 | 6.1 | 6.5 | 6.4 | 6.3 | 6.2 | 6.1 |
| | Median | 7.2 | 7.2 | 7.1 | 7.2 | 7.1 | 7.4 | 7.3 | 7.2 | 7.2 | 7.1 |
| | Max | 8.3 | 8.3 | 8.2 | 8.3 | 8.3 | 8.4 | 8.4 | 8.3 | 8.3 | 8.2 |
| TRIG | Min | 37.28 | 38.2 | 40.26 | 44.79 | 49.07 | 40.85 | 44.79 | 46.74 | 47.9 | 47.97 |
| | Median | 97.09 | 98.56 | 103.29 | 119.19 | 129.24 | 122.95 | 142.91 | 148.47 | 143.92 | 133.81 |
| | Max | 247.6 | 262.88 | 278.27 | 311.76 | 312.81 | 372.44 | 435.39 | 441.88 | 405.69 | 349.43 |
| FRUC | Min | 1.3 | 1.3 | 1.3 | 1.3 | 1.4 | 1.4 | 1.4 | 1.4 | 1.4 | 1.4 |
| | Median | 1.6 | 1.63 | 1.64 | 1.7 | 1.7 | 1.7 | 1.7 | 1.7 | 1.7 | 1.7 |
| | Max | 2.1 | 2.1 | 2.23 | 2.5 | 2.6 | 2.12 | 2.23 | 2.5 | 2.7 | 2.6 |
| GLOB | Min | 1.9 | 1.9 | 1.9 | 1.9 | 1.9 | 1.8 | 1.8 | 1.8 | 1.8 | 1.8 |
| | Median | 2.7 | 2.7 | 2.7 | 2.7 | 2.7 | 2.6 | 2.6 | 2.6 | 2.6 | 2.6 |
| | Max | 3.7 | 3.7 | 3.8 | 3.9 | 3.9 | 3.5 | 3.6 | 3.6 | 3.7 | 3.7 |
| HDL | Min | 33 | 33 | 33 | 33 | 33 | 26 | 26 | 26 | 27 | 27 |
| | Median | 59 | 59 | 60 | 62 | 61 | 47 | 47 | 48 | 49 | 49 |
| | Max | 100 | 100 | 104 | 110 | 111 | 81 | 82 | 86 | 89 | 91 |
| CHOL_HDL | Min | 1.85 | 1.87 | 1.87 | 1.91 | 1.92 | 2.07 | 2.2 | 2.22 | 2.16 | 2.05 |
| | Median | 2.97 | 3.06 | 3.15 | 3.29 | 3.27 | 3.74 | 4.12 | 4.16 | 4 | 3.73 |
| | Max | 5.83 | 6.09 | 6.36 | 6.61 | 6.54 | 7.89 | 8.32 | 8.26 | 7.81 | 7.24 |
| LDL | Min | 41.31 | 43.55 | 46.23 | 47.58 | 43.61 | 33.52 | 30.6 | 29.91 | 32.28 | 33.73 |
| | Median | 94.12 | 99.32 | 106.35 | 115.27 | 111.85 | 100.67 | 112.39 | 116.97 | 113.93 | 104.31 |
| | Max | 185.17 | 187.57 | 191.93 | 206.76 | 207.44 | 187.96 | 200.98 | 206.7 | 204.22 | 193.07 |

Figure 2C

| | | | | | | | | | | | | |
|---|---|---|---|---|---|---|---|---|---|---|---|---|
| LDL_HDL | Min | 0.627 | 0.652 | 0.668 | 0.693 | 0.675 | 0.709 | 0.722 | 0.702 | 0.711 | 0.699 |
| | Median | 1.61 | 1.681 | 1.765 | 1.844 | 1.794 | 2.12 | 2.363 | 2.396 | 2.292 | 2.082 |
| | Max | 3.65 | 3.785 | 3.948 | 4.113 | 4.072 | 4.669 | 4.901 | 4.899 | 4.723 | 4.446 |
| URNPH | Min | 4.66 | 4.63 | 4.58 | 4.57 | 4.56 | 4.67 | 4.64 | 4.6 | 4.57 | 4.576 |
| | Median | 5.61 | 5.56 | 5.51 | 5.48 | 5.47 | 5.63 | 5.56 | 5.52 | 5.48 | 5.478 |
| | Max | 7.91 | 7.85 | 7.74 | 7.68 | 7.68 | 7.83 | 7.71 | 7.6 | 7.48 | 7.393 |
| UPROT | Min | 1 | 1 | 1 | 1 | 1 | 1 | 1 | 1 | 1 | 1 |
| | Median | 10 | 10 | 9 | 8 | 8 | 10 | 9 | 9 | 9 | 9 |
| | Max | 26 | 24 | 23 | 22 | 25 | 24 | 23 | 23 | 24 | 28 |
| UCREAT | Min | 11.6 | 10.8 | 10.3 | 10.2 | 10.5 | 13 | 13.2 | 13.4 | 14.1 | 15.7 |
| | Median | 131.1 | 120.1 | 109.1 | 95.5 | 89 | 160.9 | 150.9 | 140.6 | 131.8 | 124.9 |
| | Max | 358.9 | 341 | 328.2 | 307.7 | 299.5 | 398.6 | 380.3 | 362.5 | 345.8 | 331.9 |
| UPROT_CREAT | Min | 0.031 | 0.031 | 0.03 | 0.029 | 0.031 | 0.024 | 0.024 | 0.024 | 0.025 | 0.027 |
| | Median | 0.083 | 0.084 | 0.085 | 0.089 | 0.095 | 0.064 | 0.066 | 0.069 | 0.072 | 0.077 |
| | Max | 0.209 | 0.214 | 0.222 | 0.228 | 0.261 | 0.147 | 0.154 | 0.167 | 0.182 | 0.223 |
| BMI | Min | 17.1 | 17.59 | 18.01 | 18.27 | 17.97 | 18.34 | 19.53 | 20.08 | 20.22 | 19.93 |
| | Median | 23.77 | 24.51 | 25.24 | 26.44 | 26.56 | 26.12 | 27.05 | 27.44 | 27.76 | 27.61 |
| | Max | 43.25 | 44.1 | 44.28 | 44.95 | 43.77 | 41.5 | 41.84 | 41.72 | 41.77 | 40.89 |
| Pulse | Min | 53 | 53 | 52 | 52 | 52 | 50 | 51 | 50 | 50 | 48.5 |
| | Median | 69 | 68 | 68 | 68 | 68 | 68 | 68 | 68 | 68 | 68 |
| | Max | 93.5 | 91 | 90 | 90 | 92 | 89 | 89 | 89.5 | 90 | 90 |
| AST_ALT | Min | 0.539 | 0.543 | 0.555 | 0.545 | 0.595 | 0.412 | 0.418 | 0.443 | 0.483 | 0.543 |
| | Median | 1.261 | 1.226 | 1.198 | 1.123 | 1.183 | 0.966 | 0.896 | 0.895 | 0.938 | 1.042 |
| | Max | 2.862 | 2.746 | 2.645 | 2.45 | 2.575 | 2.387 | 2.148 | 2.068 | 2.089 | 2.295 |
| ALB_PROT | Min | 0.521 | 0.521 | 0.52 | 0.518 | 0.507 | 0.561 | 0.554 | 0.548 | 0.538 | 0.526 |
| | Median | 0.618 | 0.62 | 0.622 | 0.623 | 0.62 | 0.649 | 0.644 | 0.643 | 0.639 | 0.634 |
| | Max | 0.708 | 0.71 | 0.71 | 0.708 | 0.706 | 0.734 | 0.729 | 0.727 | 0.723 | 0.717 |
| Height | Min | 59 | 59 | 59 | 58 | 57 | 63 | 63 | 63 | 63 | 62 |
| | Median | 65 | 65 | 65 | 64 | 64 | 71 | 71 | 70 | 70 | 70 |
| | Max | 71 | 71 | 71 | 71 | 70 | 77 | 77 | 77 | 77 | 76 |

Figure 2D

| Weight | | 96 | 100 | 101 | 102 | 98 | 120 | 128 | 130 | 130 | 125 |
|---|---|---|---|---|---|---|---|---|---|---|---|
| | Min | 142 | 146 | 150 | 155 | 154 | 185 | 191 | 195 | 195 | 192 |
| | Median | 268 | 272 | 271 | 272 | 260 | 305 | 308 | 305 | 304 | 294 |
| | Max | | | | | | | | | | |
| P_Press | Lower | 15.2 | 15.18 | 15.96 | 17.92 | 21.64 | 23.94 | 23.83 | 23.91 | 25.87 | 28.02 |
| | Median | 35.3 | 35.13 | 35.74 | 38.09 | 43 | 43.71 | 42.04 | 42.8 | 45.7 | 49.67 |
| | Upper | 56.36 | 56.02 | 58.49 | 65.33 | 78.55 | 67.9 | 65.62 | 66.68 | 71.76 | 80.88 |
| ALP_GGT | Lower | 240 | 248 | 271.6 | 340.47 | 384.34 | 455.52 | 469 | 492 | 512 | 496 |
| | Median | 826.44 | 858 | 966.12 | 1387 | 1440 | 1540 | 1711 | 1843 | 1850.76 | 1696.53 |
| | Upper | 2597.66 | 3104 | 4176 | 6660.99 | 6210 | 5192 | 6401.01 | 7420 | 7503 | 6355.44 |
| ECCR | Lower | 64.93 | 60.8 | 55.01 | 48.25 | 33.56 | 76.47 | 73.1 | 66.67 | 57.88 | 41.8 |
| | Median | 113.94 | 106.86 | 97.16 | 88.38 | 72.93 | 128.26 | 121.57 | 112.03 | 101.36 | 86.15 |
| | Upper | 246.84 | 225.38 | 196.77 | 175.4 | 145.19 | 242.55 | 223.33 | 203.6 | 184.09 | 157.83 |

Figure 3A

| Gender | | Females | | | | |
|---|---|---|---|---|---|---|
| Age Range | | 20 | 30 | 40 | 50 | 60 |
| BPSYST1 | LOW | 0 | 0 | 0 | 0 | 0 |
| | HIGH | 0 | 0 | 0 | 0 | 0 |
| | TRUNC | 0 | 0.01079 | 0 | 0 | 0.00343 |
| | QUAD | 0 | 0 | 0.0003418 | 0 | 0 |
| BPDIAS1 | LOW | 0 | 0 | 0 | 0 | 0 |
| | HIGH | 0 | 0 | 0 | 0 | 0.43508 |
| | TRUNC | 0 | 0 | 0 | 0 | -0.00538 |
| | QUAD | 0 | 0 | 0 | 0.0006469 | 0 |
| ALB | LOW | 0 | 0 | 0.77635 | 0.34294 | 0.45411 |
| | HIGH | 0 | 0 | 0 | 0 | 0 |
| | TRUNC | 0 | -0.38032 | -0.41239 | 0 | -0.73367 |
| | QUAD | 0 | 0 | 0 | 0.95941 | 0 |
| ALK_PHOS | LOW | 0 | 0 | 0 | 0 | 0 |
| | HIGH | 0.78735 | 0 | 0.33277 | 0.32729 | 0 |
| | TRUNC | 0 | 0 | 0.00682 | 0.00330 | 0.00622 |
| | QUAD | 0 | 0 | 0 | 0 | 0 |
| BILI | LOW | 0 | 0 | 0 | 0 | 0 |
| | HIGH | 0 | 0 | 0 | 0 | 0 |
| | TRUNC | 0 | -0.48934 | -0.28381 | -0.30382 | 0 |
| | QUAD | 0 | 1.01754 | 0.85830 | 0.74026 | 0.41285 |
| BUN | LOW | 0 | 0 | 0.50751 | 0 | 0 |
| | HIGH | 0.91521 | 0 | 0.73789 | 0 | 0 |
| | TRUNC | 0 | 0 | 0 | -0.01599 | 0 |
| | QUAD | 0 | 0.00517 | 0 | 0.00386 | 0.00116 |
| CHOL | LOW | 0 | 0 | 0 | 0 | 0 |
| | HIGH | 0 | 0 | 0 | 0 | 0 |
| | TRUNC | 0 | 0 | 0 | -0.00330 | 0 |
| | QUAD | 0 | 0 | 0 | 0 | 0.0000261 |
| CREAT | LOW | 0.87053 | 0 | 0 | 0 | 0.55804 |
| | HIGH | 0 | 0 | 0 | 0 | 0 |
| | TRUNC | 0 | -1.67209 | 0 | 0 | 0 |
| | QUAD | 0 | 0 | 1.53734 | 1.88920 | 0.50684 |
| GGT | LOW | 0 | 0 | 0 | 0 | 0 |
| | HIGH | 0.75902 | 0 | 0 | 0 | 0 |
| | TRUNC | 0 | 0.02773 | 0.02117 | 0.02218 | 0.01757 |
| | QUAD | 0 | 0 | 0 | -0.0002122 | 0 |
| GLUC | LOW | 0 | 0 | 0 | 0 | 0 |
| | HIGH | 0 | 0 | 0 | 0 | 0 |
| | TRUNC | 0 | 0 | 0 | 0 | 0 |
| | QUAD | 0 | 0.0001495 | 0.0000499 | 0 | 0 |

Figure 3B

| | | | | | | |
|---|---|---|---|---|---|---|
| AST | LOW | 0 | 0 | 0 | 0 | 0 |
| | HIGH | 0 | 0 | 0 | 0 | -0.42391 |
| | TRUNC | 0 | -0.06718 | -0.04729 | -0.01282 | -0.01475 |
| | QUAD | 0 | 0.00185 | 0.00153 | 0.0006415 | 0.0008577 |
| ALT | LOW | 0 | 0 | 0 | 0 | 0 |
| | HIGH | 0 | 0 | 0 | 0 | 0 |
| | TRUNC | -0.01288 | 0.09341 | 0.04851 | 0 | 0 |
| | QUAD | 0 | -0.00242 | -0.00143 | 0 | 0 |
| PROT | LOW | 0 | 0 | 0 | 0.50646 | 0.55031 |
| | HIGH | 0 | 0 | 0.48779 | 0 | 0 |
| | TRUNC | 0 | 0 | 0 | -0.30986 | 0 |
| | QUAD | 0 | 0 | 0 | 0 | 0 |
| TRIG | LOW | 0 | 0 | 0 | -0.95968 | 0 |
| | HIGH | 0 | 0 | 0 | -0.25826 | 0 |
| | TRUNC | 0 | 0 | 0 | 0 | 0 |
| | QUAD | 0 | 0 | 0 | 8.00148E-6 | 0 |
| FRUC | LOW | 0 | 0 | 0 | 0 | 0 |
| | HIGH | 1.09389 | 0 | 0 | 0 | -0.44722 |
| | TRUNC | -1.05077 | -0.50593 | -0.33338 | 0 | 0 |
| | QUAD | 0 | 1.63659 | 1.53207 | 0.72376 | 0.75318 |
| GLOB | LOW | 0 | 0 | 0 | -0.52538 | 0 |
| | HIGH | 0 | 0 | 0 | 0 | 0 |
| | TRUNC | 0 | 0 | 0 | 0.22664 | 0 |
| | QUAD | 0 | 0.40436 | 0 | 0 | 0 |
| HDL | LOW | 0 | 0 | 0 | 0 | 0 |
| | HIGH | 0 | 0.83883 | 0 | 0 | 0 |
| | TRUNC | 0.03063 | 0 | 0 | 0 | -0.00619 |
| | QUAD | 0 | 0 | 0 | 0.0002383 | 0 |
| CHOL_HDL | LOW | 0 | 0 | 0 | 0 | 0 |
| | HIGH | 0 | 0 | 0 | 0 | 0.50378 |
| | TRUNC | 0 | 0 | 0 | 0 | -0.06417 |
| | QUAD | 0 | 0 | 0 | 0 | 0 |
| LDL | LOW | 1.04958 | 0 | 0 | 0 | 0 |
| | HIGH | 0 | 0 | 0 | 0 | 0 |
| | TRUNC | -0.02430 | -0.00589 | -0.00268 | 0 | 0 |
| | QUAD | 0 | 0 | 0 | 0.0000460 | 0 |
| LDL_HDL | LOW | 0 | 0 | 0 | 0 | 0 |
| | HIGH | 0 | 0 | 0 | 0 | -0.43185 |
| | TRUNC | 1.50763 | 0.23831 | 0.14972 | 0.15259 | 0 |
| | QUAD | -0.34244 | 0 | 0 | 0 | 0 |
| URNPH | LOW | 0 | 0.52026 | 0 | 0 | 0 |
| | HIGH | 0 | 0 | 0 | 0 | 0 |
| | TRUNC | 0 | 0 | 0 | 0 | 0 |
| | QUAD | 0 | 0 | 0 | 0 | 0 |

Figure 3C

| | | | | | | |
|---|---|---|---|---|---|---|
| UPROT | LOW | 0 | 0 | 0 | 0 | 0 |
| | HIGH | 0.58536 | 0 | 0 | 0.25972 | 0 |
| | TRUNC | 0 | 0.01434 | 0.04272 | 0.02267 | 0.01409 |
| | QUAD | 0 | 0 | 0 | 0 | 0 |
| UCREAT | LOW | 0.97744 | 0 | 0.66711 | 0 | 0 |
| | HIGH | 0 | 0 | 0 | 0 | 0 |
| | TRUNC | 0 | 0 | -0.00375 | -0.00173 | 0 |
| | QUAD | 0 | 0 | 0.0000140 | 0 | 0 |
| UPROT_CREAT | LOW | 0 | 0 | 0 | 0 | 0 |
| | HIGH | 0 | 0 | 0 | 0 | 0.29553 |
| | TRUNC | 0 | 0 | 0 | 0 | 6.41787 |
| | QUAD | 0 | 0 | 0 | 10.92820 | -28.82212 |
| BMI | LOW | 0.74775 | 0.54842 | 0.43114 | 0 | 0.56089 |
| | HIGH | 0 | 0 | 0 | 0 | 0 |
| | TRUNC | 0 | -0.04454 | -0.08395 | 0 | 0 |
| | QUAD | 0 | 0 | 0 | 0 | 0 |
| Pulse | LOW | 0 | 0 | 0 | 0.78507 | 0 |
| | HIGH | 0 | 0 | 0.61127 | 0 | 0 |
| | TRUNC | 0 | 0.01901 | 0 | 0.01565 | 0.00864 |
| | QUAD | 0 | 0 | 0 | 0 | 0.0005480 |
| AST_ALT | LOW | 0 | 0 | 0 | 0 | 0 |
| | HIGH | 0 | 0.88050 | 0.53130 | 0 | 0 |
| | TRUNC | 0 | 1.32994 | 0.91120 | 0.42088 | 0.47040 |
| | QUAD | 0 | -0.60193 | -0.38369 | 0 | 0 |
| ALB_PROT | LOW | 0 | 0.44263 | 0 | 0 | 0.50242 |
| | HIGH | -1.40715 | 0 | 0 | 0 | 0 |
| | TRUNC | 0 | 0 | 0 | 0 | 0 |
| | QUAD | 66.93611 | 0 | 30.73700 | 46.03556 | 0 |
| Height | LOW | 0 | 0 | 0 | 0 | 0.30511 |
| | HIGH | 0 | 0 | 0.42963 | 0 | 0 |
| | TRUNC | 0 | 0 | -0.07264 | 0 | 0.02340 |
| | QUAD | 0 | 0 | 0 | 0 | 0 |
| Weight | LOW | 0 | 0 | 0 | 0.43495 | 0 |
| | HIGH | 0.56716 | 0 | 0 | 0.53757 | 0 |
| | TRUNC | 0 | 0.01476 | 0.01536 | 0 | 0 |
| | QUAD | 0 | 0 | 0 | 0 | 0.0000704 |
| P_PRESS | LOW | 0 | 0 | 0 | 0 | 0 |
| | HIGH | 0 | 0 | 0 | 0 | 0 |
| | TRUNC | 0 | 0 | 0 | 0 | 0 |
| | QUAD | 0 | 0 | 0 | 0 | 0 |
| ALP_GGT | LOW | 0.73556 | 0 | 0 | 0 | 0 |
| | HIGH | 0 | 0.36031 | 0 | 0 | 0.29988 |
| | TRUNC | 0 | 0 | 0 | 0 | 0 |
| | QUAD | 0 | 0 | 0 | 0 | -3.9139E-8 |

Figure 3D

| | | | | | | |
|---|---|---|---|---|---|---|
| ECCR | LOW | 0.91322 | 0.66190 | 0 | 0 | 0 |
| | HIGH | 0 | 0 | 0 | 0 | 0 |
| | TRUNC | 0 | -0.01044 | 0 | 0 | -0.00402 |
| | QUAD | 0 | 0 | 0 | 0 | 0 |
| UCOT_P | | 0.59079 | 0.75595 | 0.88875 | 0.84025 | 0.71187 |
| ULEUK_P | | 0 | 0 | 0 | 0 | 0 |
| UHEMO_P | | 0 | 0 | -0.28105 | 0 | 0 |
| DIURETIC_P | | 0 | 0 | 0 | 0 | 0 |
| UGLUC_HIGH | | 1.48810 | 0.74643 | 0 | 0 | 0 |
| GLYCOLYSIS | | 0 | 0 | 0 | 0 | 0 |
| CREPROT_HIGH | | 0 | 1.26253 | 0.50914 | 0 | 0 |
| AGE | | 0 | 0.05213 | 0.06535 | 0.09220 | 0.07758 |

Figure 4A

| Gender | | Males | | | | |
|---|---|---|---|---|---|---|
| Age Range | | 20 | 30 | 40 | 50 | 60 |
| BPSYST1 | LOW | 0 | 0 | 0.43641 | 0 | 0 |
| | HIGH | 0.48409 | 0 | 0 | 0 | 0 |
| | TRUNC | 0 | 0 | 0 | 0 | 0.00453 |
| | QUAD | 0 | 0 | 0 | 0 | 0 |
| BPDIAS1 | LOW | 0 | 0 | 0.43489 | 0.35307 | 0 |
| | HIGH | 0 | 0 | 0 | 0 | 0 |
| | TRUNC | 0 | 0 | 0.01003 | 0.00506 | -0.00438 |
| | QUAD | 0.0008788 | 0.0006096 | 0 | 0 | 0.0004638 |
| ALB | LOW | 0.57131 | 0.37817 | 0.49087 | 0.36695 | 0.28478 |
| | HIGH | 0.58109 | 0 | 0 | 0 | 0 |
| | TRUNC | -0.58089 | 0 | -0.51109 | -0.46544 | 0 |
| | QUAD | 0 | 0 | 0.76511 | 0.41104 | 0.43757 |
| ALK_PHOS | LOW | 0 | 0 | 0.36028 | 0 | 0 |
| | HIGH | 0 | 0 | 0.22815 | 0.33494 | 0 |
| | TRUNC | 0.01261 | 0 | 0 | 0.00532 | 0.00949 |
| | QUAD | 0 | 0.0000816 | 0.0000770 | 0 | 0 |
| BILI | LOW | 0 | 0 | 0 | 0 | 0 |
| | HIGH | 0 | 0 | 0 | 0 | 0.30883 |
| | TRUNC | 0 | 0 | -0.38010 | 0 | 0 |
| | QUAD | 0 | 0 | 0.52269 | 0.12455 | 0 |
| BUN | LOW | 0 | 0 | 0.33382 | 0.24614 | 0.33525 |
| | HIGH | 0 | 0 | 0 | 0.29503 | 0 |
| | TRUNC | 0 | 0 | 0 | 0 | 0 |
| | QUAD | 0.00405 | 0.00589 | 0.00246 | 0.00156 | 0.00153 |
| CHOL | LOW | 0.44482 | 0 | 0.23963 | 0 | 0 |
| | HIGH | 0 | 0 | -0.32903 | 0 | 0 |
| | TRUNC | 0 | 0 | 0 | 0 | -0.00669 |
| | QUAD | 0.0000758 | 0.0000272 | 0.0000239 | 0.0000322 | 0.0000360 |
| CREAT | LOW | 0 | 0 | 0 | 0 | 0 |
| | HIGH | 0 | 0 | 0 | 0 | 0 |
| | TRUNC | 0 | -0.34856 | -0.75197 | -0.67448 | 0.57137 |
| | QUAD | 0 | 1.34719 | 1.78902 | 1.99410 | 0 |
| GGT | LOW | 0 | 0 | 0 | 0 | 0 |
| | HIGH | 0.75953 | 0 | 0.20963 | 0.20868 | 0.30423 |
| | TRUNC | 0.06193 | 0.01510 | 0.00708 | 0.01210 | 0.02311 |
| | QUAD | -0.00126 | 0 | -0.0001055 | -0.0001144 | -0.0001805 |
| GLUC | LOW | 0 | 0 | 0 | 0 | 0.39576 |
| | HIGH | 0 | 0 | 0 | 0 | 0 |
| | TRUNC | 0 | 0 | 0.00349 | 0.00281 | 0.00160 |
| | QUAD | 0.0002127 | 0.0000827 | 0 | 0 | 0 |

Figure 4B

| | | | | | | |
|---|---|---|---|---|---|---|
| AST | LOW | 0 | 0 | 0 | 0 | 0 |
| | HIGH | 0.55192 | 0 | 0 | 0 | -0.50331 |
| | TRUNC | 0 | -0.03448 | -0.01660 | -0.01315 | 0 |
| | QUAD | 0 | 0.0009555 | 0.0007282 | 0.0005203 | 0.0006183 |
| ALT | LOW | 0 | 0 | 0 | 0 | 0 |
| | HIGH | 0 | 0 | 0 | 0 | 0 |
| | TRUNC | 0 | 0.02265 | 0 | 0 | -0.02029 |
| | QUAD | 0 | -0.0003268 | 0 | 0 | 0.0006665 |
| PROT | LOW | 0 | 0 | 0 | 0 | 0 |
| | HIGH | 0 | 0 | 0 | 0 | 0 |
| | TRUNC | 0 | -0.55170 | 0 | 0 | -0.25302 |
| | QUAD | 0 | 0 | 0 | 0 | 0 |
| TRIG | LOW | 0 | 0 | 0 | 0 | 0 |
| | HIGH | 0 | 0 | 0 | 0 | 0 |
| | TRUNC | 0 | 0 | 0 | 0 | 0 |
| | QUAD | 0 | 0 | 0 | 0 | 0.00E+00 |
| FRUC | LOW | 0 | 0 | 0 | 0 | 0 |
| | HIGH | 0 | 0 | 0 | 0 | 0 |
| | TRUNC | -0.60670 | -0.31064 | -0.47953 | 0 | 0 |
| | QUAD | 0 | 1.26857 | 0.85732 | 0.39018 | 0.42240 |
| GLOB | LOW | 0 | 0 | 0 | 0 | 0 |
| | HIGH | 0 | 0.48184 | 0.46873 | 0.26950 | 0.23848 |
| | TRUNC | 0 | 0.39751 | 0 | 0 | 0 |
| | QUAD | 0 | 0 | 0 | 0 | 0.21820 |
| HDL | LOW | 0 | 0 | 0 | 0 | 0 |
| | HIGH | 0 | 0 | 0 | 0 | 0 |
| | TRUNC | 0 | 0 | 0 | -0.01481 | 0.01305 |
| | QUAD | 0 | 0.0003254 | 0.0002396 | 0.0002982 | 0 |
| CHOL_HDL | LOW | 0 | 0 | 0 | 0.29321 | 0 |
| | HIGH | 0 | 0 | 0 | 0 | 0 |
| | TRUNC | 0 | -0.04504 | 0 | -0.12517 | 0.26724 |
| | QUAD | 0 | 0 | 0 | 0 | -0.02775 |
| LDL | LOW | 0 | -0.53261 | 0 | -0.23293 | 0 |
| | HIGH | 0 | 0.31176 | 0 | 0 | 0 |
| | TRUNC | 0 | 0 | 0 | 0.00231 | 0 |
| | QUAD | -0.0000986 | 0 | 0 | 0 | 0 |
| LDL_HDL | LOW | 0 | 0 | 0 | 0 | 0 |
| | HIGH | 0 | 0 | 0 | -0.25685 | 0.26896 |
| | TRUNC | -0.15944 | 0 | 0.06105 | 0 | 0 |
| | QUAD | 0.07697 | 0 | 0 | 0.05137 | 0 |

Figure 4C

| | | | | | | |
|---|---|---|---|---|---|---|
| URNPH | LOW | 0 | 0 | 0 | 0 | 0 |
| | HIGH | 0 | 0 | 0 | 0.32134 | 0 |
| | TRUNC | 0 | 0 | 0 | -0.08516 | -0.11967 |
| | QUAD | 0 | 0 | 0 | 0 | 0.07929 |
| UPROT | LOW | 0 | 0 | 0 | 0 | 0 |
| | HIGH | 0 | 0 | 0.20561 | 0 | 0.25733 |
| | TRUNC | 0.01309 | 0 | 0 | 0.03701 | 0.03009 |
| | QUAD | 0 | 0 | 0 | 0 | -0.00146 |
| UCREAT | LOW | 0 | 0 | 0 | 0 | 0 |
| | HIGH | 0 | 0 | 0 | 0 | 0 |
| | TRUNC | 0 | 0 | 0 | -0.00264 | -0.00188 |
| | QUAD | 0 | 0 | 0 | 6.96502E-6 | 0 |
| UPROT_CREAT | LOW | 0 | 0 | 0 | 0 | 0 |
| | HIGH | 0 | 0 | 0 | 0 | 0 |
| | TRUNC | 0 | 4.65207 | 3.71001 | 0 | 1.87297 |
| | QUAD | 57.86052 | 0 | 0 | 0 | 0 |
| BMI | LOW | 0 | 0.49785 | 0 | 0.50327 | 0.43586 |
| | HIGH | 0 | 0 | 0 | 0.35717 | 0 |
| | TRUNC | 0 | 0 | -0.02665 | -0.01709 | 0.05704 |
| | QUAD | 0 | 0 | 0.00167 | 0 | 0.00288 |
| Pulse | LOW | 0 | 0 | 0 | 0.40261 | 0 |
| | HIGH | 0 | 0 | 0 | 0.27107 | 0 |
| | TRUNC | 0 | 0.01353 | 0.00975 | 0.01155 | 0.01252 |
| | QUAD | 0.0006845 | 0 | 0 | 0 | 0 |
| AST_ALT | LOW | 0 | 0 | 0 | 0 | -0.50560 |
| | HIGH | 0 | 0 | 0 | 0 | 0 |
| | TRUNC | 0.60361 | 1.16376 | 0.56191 | 0.57693 | 0.47456 |
| | QUAD | -0.36282 | -0.67060 | 0 | 0 | -0.32542 |
| ALB_PROT | LOW | 0.67277 | 0.49600 | 0 | 0 | 0 |
| | HIGH | 0.46731 | 0 | 0 | 0 | 0 |
| | TRUNC | 0 | 0 | 0 | 0 | -3.85210 |
| | QUAD | 0 | 0 | 0 | 27.39984 | 0 |
| Height | LOW | 0 | 0 | 0 | 0 | 0 |
| | HIGH | 0 | 0 | 0 | 0 | 0 |
| | TRUNC | 0 | 0 | 0 | 0 | 0.05117 |
| | QUAD | 0 | 0 | 0 | 0 | 0 |
| Weight | LOW | 0 | 0 | 0.35356 | 0 | 0 |
| | HIGH | 0 | 0 | 0 | 0 | 0 |
| | TRUNC | 0 | 0.00303 | 0.00491 | 0.00547 | -0.01081 |
| | QUAD | 0 | 0 | 0 | 0 | 0 |
| P_PRESS | LOW | 0 | 0 | 0 | 0 | 0 |
| | HIGH | 0 | 0 | 0 | 0 | 0 |
| | TRUNC | 0 | 0 | 0.00872 | 0.00981 | 0 |
| | QUAD | 0 | 0.0004899 | 0 | 0 | 0 |

Figure 4D

| ALP_GGT | LOW | 0 | 0 | 0 | 0 | 0 |
|---|---|---|---|---|---|---|
| | HIGH | 0 | 0.48586 | 0 | 0 | 0 |
| | TRUNC | -0.0005023 | 0.0001243 | 0.0000939 | 0 | -0.0001397 |
| | QUAD | 9.54728E-8 | -4.6816E-8 | 0 | 0 | 0 |
| ECCR | LOW | 0 | 0 | 0 | 0.23334 | 0 |
| | HIGH | 0 | 0 | 0 | -0.23271 | 0 |
| | TRUNC | 0 | 0 | 0 | 0 | 0.00774 |
| | QUAD | 0 | 0 | 0 | 0 | 0 |
| UCOT_P | | 0.67237 | 0.66018 | 0.65499 | 0.73324 | 0.61250 |
| ULEUK_P | | 0 | 0 | 0 | 0 | 0 |
| UHEMO_P | | 0 | 0.25656 | 0 | 0 | 0.16775 |
| DIURETIC_P | | 0 | 0.46184 | 0.20611 | 0 | 0 |
| UGLUC_HIGH | | 0 | 0 | 0 | -0.20137 | 0 |
| GLYCOLYSIS | | 0 | 0 | 0.08512 | 0 | 0 |
| CREPROT_HIGH | | 0 | 0 | 0 | 0 | 0 |
| AGE | | -0.04714 | 0.05467 | 0.06201 | 0.06602 | 0.09149 |

Figure 5A

| SEX | Females | | Males | |
|---|---|---|---|---|
| COT_P | 0 | 1 | 0 | 1 |
| 18 | 1.166311 | 2.2832401 | 0.08667 | 0.185391 |
| 19 | 1.163228 | 2.3628788 | 0.078602 | 0.169216 |
| 20 | 1.170347 | 2.3786583 | 0.072315 | 0.15682 |
| 21 | 1.163916 | 2.3360975 | 0.068043 | 0.14992 |
| 22 | 1.147632 | 2.3678914 | 0.062991 | 0.138702 |
| 23 | 1.140748 | 2.3766375 | 0.059342 | 0.129963 |
| 24 | 1.136459 | 2.3733542 | 0.05633 | 0.12196 |
| 25 | 1.134469 | 2.3626518 | 0.053595 | 0.117441 |
| 26 | 1.135214 | 2.3253104 | 0.050762 | 0.111165 |
| 27 | 1.136329 | 2.3340945 | 0.048453 | 0.106078 |
| 28 | 1.136561 | 2.3450209 | 0.04624 | 0.101088 |
| 29 | 1.136909 | 2.3404079 | 0.043946 | 0.097247 |
| 30 | 10.01619 | 26.450602 | 3.19783 | 7.317526 |
| 31 | 10.65557 | 28.166354 | 3.40148 | 7.85735 |
| 32 | 11.35772 | 30.212273 | 3.630159 | 8.496285 |
| 33 | 12.13086 | 31.974057 | 3.871314 | 9.02854 |
| 34 | 12.99273 | 34.231085 | 4.157689 | 9.705774 |
| 35 | 13.92273 | 37.155868 | 4.450235 | 10.43198 |
| 36 | 14.80698 | 39.316519 | 4.769577 | 11.29652 |
| 37 | 15.90408 | 42.516604 | 5.09869 | 12.09942 |
| 38 | 16.96174 | 45.776094 | 5.450691 | 12.87698 |
| 39 | 18.24529 | 48.643425 | 5.820543 | 13.78344 |
| 40 | 0.089762 | 0.2606957 | 6.751586 | 16.57241 |
| 41 | 0.096569 | 0.2817959 | 7.271574 | 18.10776 |
| 42 | 0.103715 | 0.303931 | 7.822505 | 19.44915 |
| 43 | 0.11092 | 0.3235623 | 8.406601 | 21.35346 |
| 44 | 0.118723 | 0.3533538 | 8.979298 | 22.83984 |
| 45 | 0.128593 | 0.3822781 | 9.668357 | 24.87861 |
| 46 | 0.13913 | 0.4156601 | 10.50649 | 26.98595 |
| 47 | 0.149896 | 0.4478019 | 11.27528 | 29.24691 |
| 48 | 0.162014 | 0.4764818 | 12.11377 | 31.61854 |
| 49 | 0.17518 | 0.5223445 | 13.03812 | 33.70631 |
| 50 | 119.0263 | 341.09561 | 16.36892 | 42.93476 |
| 51 | 132.3538 | 391.2495 | 17.73957 | 46.20905 |
| 52 | 145.7733 | 425.62877 | 19.17367 | 51.04079 |
| 53 | 160.0701 | 458.43625 | 20.77221 | 54.73998 |
| 54 | 174.8938 | 517.46122 | 22.36676 | 59.1409 |
| 55 | 191.5597 | 562.86474 | 24.14821 | 64.13113 |
| 56 | 211.1005 | 619.09879 | 26.18973 | 69.50065 |
| 57 | 234.2761 | 701.09882 | 28.40641 | 75.20702 |
| 58 | 257.9954 | 761.59692 | 30.68027 | 83.63563 |
| 59 | 285.1868 | 859.85019 | 33.21497 | 87.4939 |
| 60 | 97.62178 | 255.61264 | 3355.781 | 8300.12 |

Figure 5B

| | | | | |
|---|---|---|---|---|
| 61 | 108.1147 | 283.96328 | 3719.161 | 9163.379 |
| 62 | 119.7355 | 315.45836 | 4121.889 | 10116.42 |
| 63 | 132.6054 | 350.44665 | 4568.227 | 11168.58 |
| 64 | 146.8585 | 389.31557 | 5062.897 | 12330.18 |
| 65 | 162.6437 | 432.49554 | 5611.131 | 13612.59 |
| 66 | 180.1256 | 480.46472 | 6218.731 | 15028.37 |
| 67 | 199.4865 | 533.75427 | 6892.125 | 16591.4 |
| 68 | 220.9284 | 592.95431 | 7638.437 | 18317 |
| 69 | 244.6751 | 658.72036 | 8465.563 | 20222.07 |
| 70 | 270.9741 | 731.7807 | 9382.254 | 22325.28 |
| 71 | 300.1 | 812.94435 | 10398.21 | 24647.23 |
| 72 | 332.3564 | 903.11006 | 11524.18 | 27210.68 |
| 73 | 368.08 | 1003.2763 | 12772.07 | 30040.74 |
| 74 | 407.6433 | 1114.5522 | 14155.09 | 33165.14 |
| 75 | 451.4591 | 1238.17 | 15687.87 | 36614.5 |
| 76 | 499.9845 | 1375.4985 | 17386.63 | 40422.61 |
| 77 | 553.7256 | 1528.0586 | 19269.33 | 44626.78 |
| 78 | 613.2432 | 1697.5394 | 21355.91 | 49268.21 |
| 79 | 679.158 | 1885.8178 | 23668.43 | 54392.38 |

METHODS FOR ESTIMATING MORTALITY RISK OF AN INDIVIDUAL AMONG A PEER GROUP

CROSS-REFERENCE TO RELATED APPLICATIONS

This application claims the benefit of U.S. patent application Ser. No. 13/340,541, filed Dec. 29, 2011, which in turn claims the benefit of U.S. Provisional Application Ser. No. 61/428,597, filed Dec. 30, 2010, the contents of both of which are hereby incorporated by reference in their entireties.

FIELD

The invention relates to methods for estimating mortality risk of an individual among a peer group. The individuals estimated mortality risk may be used, for example, in underwriting an insurance policy.

BACKGROUND

The following description of the background of the invention is provided simply as an aid in understanding the invention and is not admitted to describe or constitute prior art to the invention.

Insurance underwriting involves evaluating risk exposure of potential clients to determine the premium to be charged to insure that risk. As part of the underwriting process for life or health insurance, medical underwriting, a process which considers indicators of present or future medical condition, may be used to examine the applicant's health status and estimate the applicant's mortality risk.

Laboratory tests have long been recognized as having implications on the mortality risk of the individual tested, and in fact, medical underwriters have long utilized laboratory tests in estimating a mortality risk for an individual. Generally, these assessments are based on individual assays, or at most, restricted groups of closely related assays (such as the group of total cholesterol and high density lipoprotein (HDL), or the group of aspartate aminotransferase (AST), alanine aminotransferase (ALT), and gamma-glutamyl transferase (GGT)).

SUMMARY

The present invention provides methods for estimating the mortality risk of an individual compared to a peer group and its methods of use.

One embodiment of the invention provides methods of determining the relative mortality risk of an individual. In some aspects, the methods comprise calculating multivariate model input variables from a plurality of raw variables selected from physical characteristics and/or the levels of analytes determined in one or more body fluids from said individual, and determining relative mortality risk using said model input variables in a multivariate model having predetermined coefficients. One or more steps of the methods, in one aspect, is performed by a computer. In another aspect, the determination result is output to a user or computer readable format and/or a non-transitory computer-readable media.

In one aspect, the multivariate model is a Cox proportional hazards multivariate regression model. In one aspect, the predetermined coefficients are determined using physical characteristics and analyte levels from a plurality of individuals.

In some aspects, the plurality of raw variables comprise at least two, or alternatively three, four, five, six, seven, eight, nine, ten or more raw variables. In one aspect, the plurality of raw variables comprise at least one, two, three, four, five or more physical characteristics and one, two, three, four, five, or more analyte levels.

In some aspects, the calculation of the multivariate model input variables comprises truncating one or more said raw variables between a maximum level and a minimum level. In certain aspects, the calculation of said multivariate model input variables further comprises generating a variation input variable, for each of said one or more raw variables, measuring the difference between said raw variable, or the truncated level thereof, and a median level.

In one aspect, said maximum, minimum and median levels are determined from a plurality of individuals. In another aspect, said calculation and determination are stratified by the age and gender of said individual.

In certain aspects, said physical characteristics are one, two, three, four, five or more selected from the group consisting of age, sex, height, weight, diastolic blood pressure, systolic blood pressure, pulse, and body mass index. In a particular aspect, said physical characteristics comprise all of age, sex, height, weight, diastolic blood pressure, systolic blood pressure, pulse, and body mass index.

In one aspect, said analytes are one, two, three, four, five, six, seven, eight, nine, ten or more selected from the group consisting of Albumin (ALB), Alkaline Phosphatase (ALP), Alanine Aminotransferase (ALT), Aspartate Aminotransferase (AST), Bilirubin (BILI), Blood Urea Nitrogen (BUN), Cholesterol (CHOL), Urine Hydrochlorothiazide (Diuretic), Fructosamine (FRUC), Gamma-glutamyl Transferase (GGT), Blood sugar (GLUC), High Density Liporproteins (HDL), Total Protein (PROT), Triglycerides (TRIG), Urine Cotinine (UCOT), Urine Creatinine (UCREAT), Urine Glucose (UGLUC), Urine Hemosiderin (UHEMO), Urine Protein (UPROT), Urine pH (URNPH), Creatinine (CREAT), Urine Leukocyte Esterase (ULEUK), Urine Cocaine (UCOC), and Blood HIV (BLDHIV).

In another aspect, said analytes comprise all of Albumin (ALB), Alkaline Phosphatase (ALP), Alanine Aminotransferase (ALT), Aspartate Aminotransferase (AST), Bilirubin (BILI), Blood Urea Nitrogen (BUN), Cholesterol (CHOL), Urine Hydrochlorothiazide (Diuretic), Fructosamine (FRUC), Gamma-glutamyl Transferase (GGT), Blood sugar (GLUC), High Density Liporproteins (HDL), Total Protein (PROT), Triglycerides (TRIG), Urine Cotinine (UCOT), Urine Creatinine (UCREAT), Urine Glucose (UGLUC), Urine Hemosiderin (UHEMO), Urine Protein (UPROT), Urine pH (URNPH), Creatinine (CREAT), Urine Leukocyte Esterase (ULEUK), Urine Cocaine (UCOC), and Blood HIV (BLDHIV).

In some aspects, the values of said coefficients are within the ranges of the values shown in Tables 2-3 and FIGS. 2A-5B±20%. In some aspects, the values of said coefficients are within the ranges of the values shown in Tables 2-3 and FIGS. 2A-5B±10%.

In a particular aspect, the relative mortality risk is scaled to 100.

Also provided, in another embodiment, is a method of underwriting a life or medical insurance policy for an individual, comprising determining a relative mortality risk of an individual by the method of any of the above embodiments or aspects, and determining a price for said life or medical insurance policy based on said relative mortality risk of the individual.

The term "model" as used herein refers to a mathematical or logical representation of a system of entities, phenomena, or processes. Implementation of a model may include deriving values of mathematical parameters contained within the model. Values of model parameters may be derived by any appropriate mathematical method known in the art.

The term "reflex test" as used herein is a test that is or is not performed based on the results of earlier testing. A reflex test may be performed to provide additional information which would help interpret the findings of the prior testing. For example, if a individual's initial physical characteristics and biological fluid analyte levels are inconclusive as to which risk category the individual should be placed for insurance underwriting purposes, reflex testing, such as analysis for an analyte not initially determined, may be conducted to provide data regarding an additional risk factor. In some embodiments, prostate specific antigen (PSA) may be determined as a reflex test.

The term "about" as used herein in reference to quantitative measurements refers to the indicated value plus or minus 10%.

The summary of the invention described above is non-limiting and other features and advantages of the invention will be apparent from the following detailed description of the invention, and from the claims.

BRIEF DESCRIPTION OF THE DRAWINGS

FIGS. 2A-2D provides exemplary Input Variable Constants for estimating relative mortality risk according some embodiments of the present invention. For age ranges, 20 represents 18-29, 30 represents 30-39, 40 represents 40-49, 50 represents 50-59, and 60 represents 60-79.

FIGS. 3A-3D and FIGS. 4A-4D provide exemplary Model Input Variable Coefficients (13) for females and males, respectively, for estimating mortality risk according to some embodiments of the present invention. For age ranges, 20 represents 18-29, 30 represents 30-39, 40 represents 40-49, 50 represents 50-59, and 60 represents 60-79.

FIGS. 5A-5B provide exemplary Age Adjustment Factors for estimating mortality risk according to some embodiments of the present invention. For age ranges, 20 represents 18-29, 30 represents 30-39, 40 represents 40-49, 50 represents 50-59, and 60 represents 60-79.

DETAILED DESCRIPTION

Figure 1:
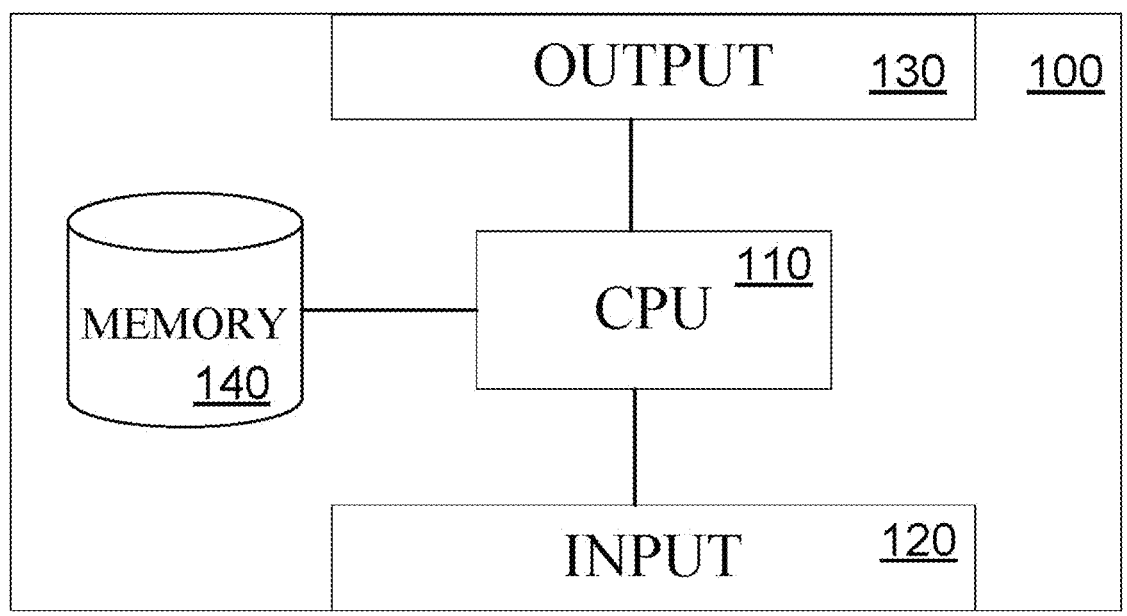
FIG. 1 is a schematic illustration of a process overview for estimating relative mortality risk of an individual.

Presented herein are methods for determining the mortality risk of an individual among a peer group which utilize multivariate analysis. These methods utilize interrelationships of laboratory and physical variables to determine an individual's mortality risk for individual-level risk stratification.

The usefulness of individual-level risk stratification has been severely limited by the pervasive cross-correlation of numerous laboratory measured analytes and physical characteristics. Interrelationship of variables under consideration invariably afflicts all univariate (i.e., single variable) and limited multivariate (i.e., few variable) analyses with two closely associated shortcomings: cross-attribution of effects and non-additivity of results.

For example, Body Mass Index (BMI), is strongly correlated with albumin (ALB), alkaline phosphatase (ALP), blood pressure (diastolic and systolic), pulse, triglycerides (TRIG), the aspartate aminotransferase (AST)/alanine aminotransferase (AST) ratio, bilirubin (BILI), gamma-glutamyl transferase (GGT), and the Cholesterol (CHOL)/high density lipoprotein (HDL) ratio. Thus, any analysis of the relationship between BMI and mortality which does not explicitly control for the effects of the other correlated variables (as well as others with a weaker, but statistically significant relationship to BMI) will implicitly attribute much of the risk derived from the other correlated variables to BMI per se. Conversely, univariate analysis of any of the correlated variables will confound the consequences of abnormal BMI with that of the attribute under study. This is cross-attribution, the crediting of the effects of correlated variables solely to the test or measurement under consideration.

Non-additivity follows directly from this effect; it is impossible for an underwriter to apply the conclusions of separate univariate studies of correlated variables without partially "double-counting" the effects of each test. Non-additivity is particularly troublesome as virtually all common laboratory tests and physical measurements are correlated to a statically significant degree. Failure to account for non-additivity of the risk attributed to individual variables under consideration leads to an overestimate of the mortality risk of the individual.

In order to more precisely model mortality risk by allowing for the very different implications of many variables according to age and gender, the methods presented herein utilize 10 independent stratum models—one for each of five age ranges (18-29, 30-39, 40-49, 50-59, and 60-79) per gender; with final rankings within each stratum model further subdivided by tobacco use (e.g., as indicated by urinary cotinine (UCOT) status (<0.3, >0.3 µg/ml)).

Each stratum model is constructed by Cox proportional hazards multivariate regression, and incorporates several "raw" variables (including results from a plurality of the laboratory tests listed in Table 1), as well as a variety of variables calculated from results of two or more laboratory tests, and various synthetic variables designed to permit the modeling of non-linear relationships between results/measurements and mortality risk (i.e., the detection of "J-shaped", "U-shaped", and other non-linear relationships). No individual variable is included in a given stratum model unless its p-value within that context is less than 0.05.

Measured Variables.

A plurality of variables used in methods presented herein are raw data derived from laboratory testing for the amount of a biochemical species in a sample from an individual, and/or are raw data from measurement of various physical attributes of the individual. Laboratory tests may be used to determine the levels of one or more desired biochemical species in a bodily fluid, such as blood, plasma, serum, urine, or the like. The specific laboratory tests used to determine the levels of the desired biochemical species may be any suitable laboratory test known in the art. Measurement of various physical characteristics (such as sex, age, height, weight, diastolic and systolic blood pressures, pulse, and body mass index) do not require laboratory testing. Instead, some of these characteristics may be provided by the individual, or be measured by a suitable health care provider. Table 1 lists several exemplary physical characteristics and laboratory determined analytes that have been considered in developing the instant methods.

TABLE 1

Exemplary Laboratory and Physical Measurements

| | |
|---|---|
| Age | Fructosamine (FRUC) |
| Sex | Gamma-glutamyl Transferase (GGT) |
| Height | Blood sugar (GLUC) |
| Weight | High Density Liporproteins (HDL) |
| Systolic Pressure (BPSYST) | Total Protein (PROT) |
| Diastolic Pressure (BPDIAS) | Triglycerides (TRIG) |
| PULSE | Urine Cotinine (UCOT) |
| Body Mass Index (BMI) | Urine Creatinine (UCREAT) |
| Albumin (ALB) | Urine Glucose (UGLUC) |
| Alkaline Phosphatase (ALP) | Urine Hemosiderin (UHEMO) |
| Alanine Aminotransferase (ALT) | Urine Protein (UPROT) |
| Aspartate Aminotransferase (AST) | Urine pH (URNPH) |
| Bilirubin (BILI) | Creatinine (CREAT) |
| Blood Urea Nitrogen (BUN) | Urine Leukocyte Esterase (ULEUK) |
| Cholesterol (CHOL) | Urine Cocaine (UCOC) |
| Urine Hydrochlorothiazide (Diuretic) | Blood HIV (BLDHIV) |

In certain embodiments, one or more of the variables used in a multivariate mortality risk estimate may be adjusted for empirically observed seasonal variances. For example, one or more of BPSYST, BPDIAS, ALT, GLUC, TRIG, and URNPH may be adjusted according to the general formula:

$$VAR\_ADJ = VAR/FACTOR \quad (1)$$

where: VAR_ADJ is the adjusted variable;

VAR is the measured value; and

FACTOR is calculated according to the formula:

$$FACTOR = SIN\_CONST*DATE\_SIN + COS\_CONST*DATE\_COS + INTERCEPT; \quad (2)$$

where:

$$DATE\_SIN = SIN(2\pi*DAY/365); \quad (3)$$

$$DATE\_COS = COS(2\pi*DAY/365); \quad (4)$$

DAY=day of the year (e.g., January 5=5; February 1=32; etc.);

and SIN_CONST, COS_CONST, and INTERCEPT are determined empirically.

As indicated above, the variables SIN_CONST, COS_CONST, and INTERCEPT are determined empirically for use in the seasonal adjustments. Exemplary values for these variables are presented in Tables 2 and 3 for females and males, respectively. Typically, values for these constants will fall within the range of the indicated values ±20%.

TABLE 2

Exemplary SIN_CONSTANT, COS_CONST, and INTERCEPT values for females

| | Females | | |
|---|---|---|---|
| Variable | SIN_CONST | COS_CONST | INTERCEPT |
| BPSYST | 0.00201 | 0.00507 | 0.99835 |
| BPDIAS | 0.00151 | 0.00502 | 0.93318 |
| ALT | 0.01033 | 0.0263 | 1.00176 |
| GLUC | 0.00453 | 0.00766 | 1.00079 |
| TRIG | −0.01369 | −0.01462 | 0.97847 |
| URNPH | −0.00702 | −0.01401 | 1.00186 |

TABLE 3

Exemplary SIN_CONST, COS_CONST, and INTERCEPT values for males

| | Males | | |
|---|---|---|---|
| Variable | SIN_CONST | COS_CONST | INTERCEPT |
| BPSYST | 0.00193 | 0.00484 | 0.99993 |
| BPDIAS | 0.00165 | 0.00523 | 0.99869 |
| ALT | 0.01866 | 0.04768 | 1.02896 |
| GLUC | 0.00549 | 0.01024 | 1.00008 |
| TRIG | −0.015 | −0.00538 | 0.97426 |
| URNPH | −0.00707 | −0.01348 | 1.00025 |

Calculated Variables.

As indicated above, a variety of variables calculated from results of two or more laboratory tests may also be used in the methods described herein. These include the variables listed in Table 4.

TABLE 4

Exemplary Calculated Variables

Globulins (GLOB)
Albumin Fraction (ALB_PROT)
AST: ALT Ratio (AST_ALT)
Low Density Lipoproteins (LDL)
Cholesterol: HDL Ratio (CHOL_HDL)
LDL: HDL Ratio (LDL_HDL)
Urinary Protein: Urinary Creatinine Ratio (UPROT_CREAT)
BPSYST BPDIAS differential (P_PRESS)
ALP × GGT (ALP_GGT)
Estimated Creatinine Clearance (eCCr)

The calculated variables listed in Table 4 are defined as follows:

$$GLOB = PROT - ALB; \quad (5)$$

$$ALB\_PROT = ALB/PROT; \quad (6)$$

$$AST\_ALT = AST/ALT; \quad (7)$$

$$LDL = CHOL - HDL - TRIG/5; \quad (8)$$

$$CHOL\_HDL - CHOL/HDL; \quad (9)$$

$$LDL\_HDL = LDL/HDL; \quad (10)$$

$$UPROT\_CREAT = UPROT/UCREAT; \quad (11)$$

$$P\_PRESS = BPSYST - BPDIAS \text{(using seasonally corrected values)}; \quad (12)$$

$$ALP\_GGT = ALK\_PHOS*GGT; \text{ and} \quad (13)$$

eCCr=

$$eCCr=(140-AGE)*(WEIGHT/2.2)/(72*CREAT)\text{(for male)}, \text{ or}$$

$$eCCr=0.85*(140-AGE)*(WEIGHT/2.2)/(72*CREAT)\text{(for female)}. \quad (14)$$

Model Input Variables.

The above Measured and Calculated Variables are used to generate two types of Model Input Variables: Quantitative Input Variables, and Qualitative Input Variables. The Model Input Variables are determined by comparison of the Measured and Calculated Variable values to Input Variable Constants. The Input Variable Constants used for each Model Input Variable vary by sex and age of the individual, as well as the variable under consideration. Exemplary Input Variable Constants are provided in FIGS. 2A-2D.

Input Variable Constants used in methods presented herein may be determined by any suitable mathematical method known in the art, including for example by empirical analysis of the distribution of variable values in reference populations. The Exemplary Input Variable Constants presented in FIGS. 2A-2D were derived from physical characteristics and body fluid analyte levels from about 5.95 million insurance applicants, but may be subject to further refinement if the applicant pool is modified or expanded. It is expected, however, that the Exemplary Input Variable Constants will generally fall within the range of the values presented in FIGS. 2A-2D±20%; such as ±10%.

A. Quantitative Model Input Variables:

Quantitative Model Input Variables are determined as follows:

Each of the Measured and Calculated Variables is used to generate four Model Input Variables: VAR-LOW, VAR-_HIGH, VAR_TRUNC, and VAR_QUAD. Three of the Model Input Variables are determined using three Input Variable Constants (VAR_MAX, VAR_MIN, and VAR-_MEDIAN) as follows:

If VAR<VAR_MIN, then:

$$VAR\_LOW=1 \quad (15)$$

$$VAR\_HIGH=0 \quad (16)$$

$$VAR\_TRUNC=VAR\_MIN; \quad (17)$$

Else if VAR>VAR_MAX, then:

$$VAR\_LOW=0 \quad (18)$$

$$VAR\_HIGH=1 \quad (19)$$

$$VAR\_TRUNC=VAR\_MAX; \quad (20)$$

Else if VAR_MIN≤VAR≤VAR_MAX, then:

$$VAR\_LOW=0 \quad (21)$$

$$VAR\_HIGH=0 \quad (22)$$

$$VAR\_TRUNC=VAR. \quad (23)$$

The final Model Input Variable is determined from the equation:

$$VAR\_QUAD=(VAR\_TRUNC-VAR\_MEDIAN)^2 \quad (24)$$

B. Qualitative Model Input Variables:

Qualitative Model Input Variables are positive/negative (P/N) type variables, cutoff-based variables, or comparison-based variables.

P/N results are determined for UCOT, ULEUK, UHEMO, and DIURETIC:

If VAR='P', then VAR_P=1;
Else VAR_P=0.

Cutoff-based results are determined for UGLUC:
If UGLUC>0.25, then UGLUC_HIGH=1;
Else UGLUC_HIGH=0.

Comparison-based results are determined for CREPROT_HIGH:
If CREAT_HIGH=UPROT_CREAT_HIGH=1, then CREPROT_HIGH=1;
Else CREPROT_HIGH=0.

C. Improved Handling of Glycolysis:

A Boolean variable GLYCOLYSIS, in one aspect, is introduced, which is defined as:
If GLUCH="No Value Given (NVG)" then GLYCOLYSIS=1
Else if GLUC>0 then GLYCOLYSIS=0
If GLYCOLYSIS=0 then, calculate GLUC LOW, etc;
If GLYCOLYSIS=1 then
  GLUC LOW=0
  GLUC HIGH=0
  GLUC TRUNC=GLUC MEDIAN
  GLUC QUAD=(GLUC TRUNC)$^2$ Calculation of Raw Hazard.

Once the above Quantitative and Qualitative Model Input Variables have been determined, a Raw Hazard value is then calculated. The Raw Hazard is calculated by raising e to the power of the sum of each Model Input Variable multiplied by a coefficient determined by Cox proportional hazards multivariate regression (stratified by sex and age range):

$$HAZARD=e^{\wedge}\Sigma_{n=1}^{-122}\beta_n VAR_n \quad (25)$$

Exemplary Model Input Variable Coefficients (β) are shown in FIGS. 3A-3D and FIGS. 4A-4D for females and males, respectively.

As with the Input Variable Constants, the Model Input Variable Coefficients used in methods presented herein may be determined by any suitable mathematical method known in the art, including for example, by Cox proportional hazards multivariate regression. The Exemplary Model Input Variable Coefficients presented in FIGS. 3A-3D and FIGS. 4A-4D were developed from Cox proportional hazards multivariate regression multivariate regression of physical characteristics and body fluid analyte levels from about 5.95 million insurance applicants, but may be subject to further refinement if the applicant pool is modified or expanded. It is expected, however, that the Exemplary Model Input Variable Coefficients will generally fall within the range of the values presented in FIGS. 3A-3D and FIGS. 4A-4D±20%; such as ±10%.

Adjusted Hazard.

The Raw Hazard, derived above, is then used to determine an individual's Adjusted Hazard (or Hazard Score). The Adjusted Hazard is the ratio of the applicant's mortality risk and the median risk of other individuals in the individual's age, sex, and cotinine status, expressed as a percentage.

To calculate the Adjusted Hazard, the Raw Hazard is divided by an Age Adjustment Factor (ADJ_FACTOR), which is specific as to sex (APPSEX), age (APPAGE), date of birth (APPDOB) and cotinine status (COT P), and multiplied by 100:

$$HAZARD\_SCORE=HAZARD/ADJ\_FACTOR*100 \quad (26)$$

Exemplary Age Adjustment Factors are shown in FIGS. 5A-5B.

In one embodiment, age is calculated as AGE=(CURRENT_DATE−APPDOB)/365.25.

As with the Input Variable Constants and Model Input Variable Coefficients, Age Adjustment Factors used in methods presented herein may be determined by any suitable mathematical method known in the art, including for example, by Cox proportional hazards multivariate regression. The Exemplary Model Input Variable Coefficients presented in FIGS. 5A-5B were developed from Cox proportional hazards multivariate regression of physical characteristics and body fluid analyte levels from about 5.95 million insurance applicants, but may be subject to further refinement if the applicant pool is modified or expanded. It is expected, however, that the Exemplary Age Adjustment Factors will generally fall within the range of the values presented in FIGS. 5A-5B±20%; such as ±10%.

Variables Selected for Modeling.

The present disclosure provides various types of variables, including physical characteristics, measured analyte levels, variables calculated or derived from the physical characteristics, measured analyte levels. The disclosure further demonstrates that these variables, when used in suitable statistical models, achieve excellent results. It would be readily appreciated by the knowledgeable reader that not all such variables are required for carry out an effective estimation. Likewise, certain variables can be substituted with those not in the list without significantly impacting the performance of the estimate.

Accordingly, in one embodiment, the multivariate model input variables for the methods of the present disclosure include at least 1, or alternatively at least 2, 3, 4, 5, 6, 7, or 8 physical characteristics. In another embodiment, the multivariate model input variables for the methods of the present disclosure include at least 1, or alternatively at least 2, 3, 4, 5, 6, 7, 8, 9, 10, 11, 12, 13, 14, 15, 16, 17, 18, 19, 20, 21, 22, 23, or 24 analyte levels. In yet another embodiment, the multivariate model input variables for the methods of the present disclosure include at least 1, or alternatively at least 2, 3, 4, 5, 6, 7, 8, 9, or 10 calculated variables.

Still in another embodiment, the multivariate model input variables for the methods of the present disclosure include at least 1, or alternatively at least 2, 3, 4, 5, 6, 7, or 8 physical characteristics, and at least 1, or alternatively at least 2, 3, 4, 5, 6, 7, 8, 9, 10, 11, 12, 13, 14, 15, 16, 17, 18, 19, 20, 21, 22, 23, or 24 analyte levels. Further in another embodiment, the multivariate model input variables for the methods of the present disclosure include at least 1, or alternatively at least 2, 3, 4, 5, 6, 7, or 8 physical characteristics, at least 1, or alternatively at least 2, 3, 4, 5, 6, 7, 8, 9, 10, 11, 12, 13, 14, 15, 16, 17, 18, 19, 20, 21, 22, 23, or 24 analyte levels, and at least 1, or alternatively at least 2, 3, 4, 5, 6, 7, 8, 9, or 10 calculated variables.

Further, in one embodiment, the multivariate model input variables for the methods of the present disclosure include at least 1, or alternatively at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41 or 42 variables selected from physical characteristics, analyte levels, and/or calculated variables. In a particular embodiment, the multivariate model input variables include all variables as provided in FIGS. 2A-2D.

Mortality Risk Percentile Ranking.

The ultimate calculated output of the methods described herein is a percentile ranking of an individual's hazard score relative to the appropriate age/sex/cotinine status peer group. The possible range for this percentile ranking is, of course, 0-99, where a score of 0 indicates that fewer than 1% of peer group members present a lower mortality risk than the individual under consideration, while a 99 indicates that the individual is within the most mortality-prone 1% of his or her demographic peers. The age/sex/cotinine status normalization precludes direct comparisons of scores between groups.

This Mortality Risk Percentile Ranking may used by an insurance provider, such as a life insurance provider, to underwrite an insurance policy for an individual. As seen in the Examples below, the Mortality Risk Assessment Model overcomes limitations of univariate and limited multivariate analyses (i.e., cross-attribution and non-additivity), and accurately assesses the aggregate all-cause mortality risk of individual laboratory and physical measurement profiles. As such, the Mortality Risk Assessment Model potentially reduces underwriting requirements, identifies high-risk individuals currently underwritten as preferred, and identifies low-risk individuals currently denied preferred classification.

EXAMPLES

Example 1: Relative Death Rates by Risk Decile

The Mortality Risk Assessment Model presented herein was developed from about 5.95 million life insurance applicants for whom a complete standard laboratory and physical measurement profile was available. The earliest profiles date to late 2001, when substantial numbers of physical measurements were first captured. The current version includes individuals tested through the end of 2008. Dates of deaths were obtained from the Social Security Death Master File (SSDMF).

Figure 6:
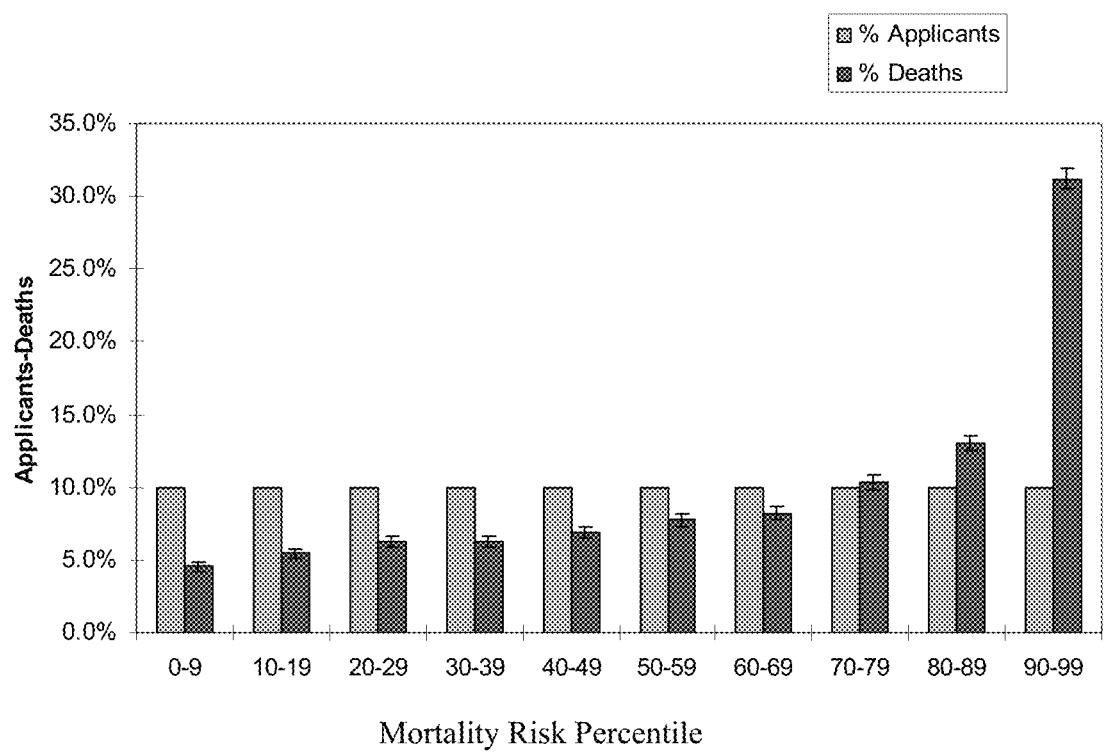
FIG. 6 shows a comparison of insurance applicants and deaths for the period of 2001-2008 according to Mortality Risk Percentile deciles. Details are discussed in Example 1.

FIG. 6 illustrates the distribution of applicants and deaths by risk decile in cotinine-negative applicants between 2001 and 2008. By design, each decile encompasses 10% of the applicant population, but the distribution of deaths is decidedly skewed. Individuals with scores of 9 or lower were 54.3% (54.0-54.6%) less likely to die during this period, while applicants scoring 90 and above were overrepresented in deaths by a factor of 3.12 (CI: 3.05-3.19).

Example 2: Absolute Death Rates by Risk Decile

After assigning Mortality Risk scores to all 5.95 million scorable applicants in the development database, 7-year mortality results were compared to the 2001 Valuation Basic Table (VBT) (published by the Society of Actuaries) select death rates for each demographic group. Results for male non-smokers 40-49 are displayed in FIG. 7, but the overall shape of this graph differed very little among strata. Although the slope of this line between Mortality Risk Assessment percentiles 0 and 74 was statistically significant, the overall impression is of comparatively flat, and distinctly low, absolute death rates in scores of roughly 74 and below. By definition, 75% of applicants lie within this ≤75 group. The mean death rate of this group was less than 60% of the VBT, a level generally considered consistent with a preferred rating by conventional underwriting standards.

Figure 7:
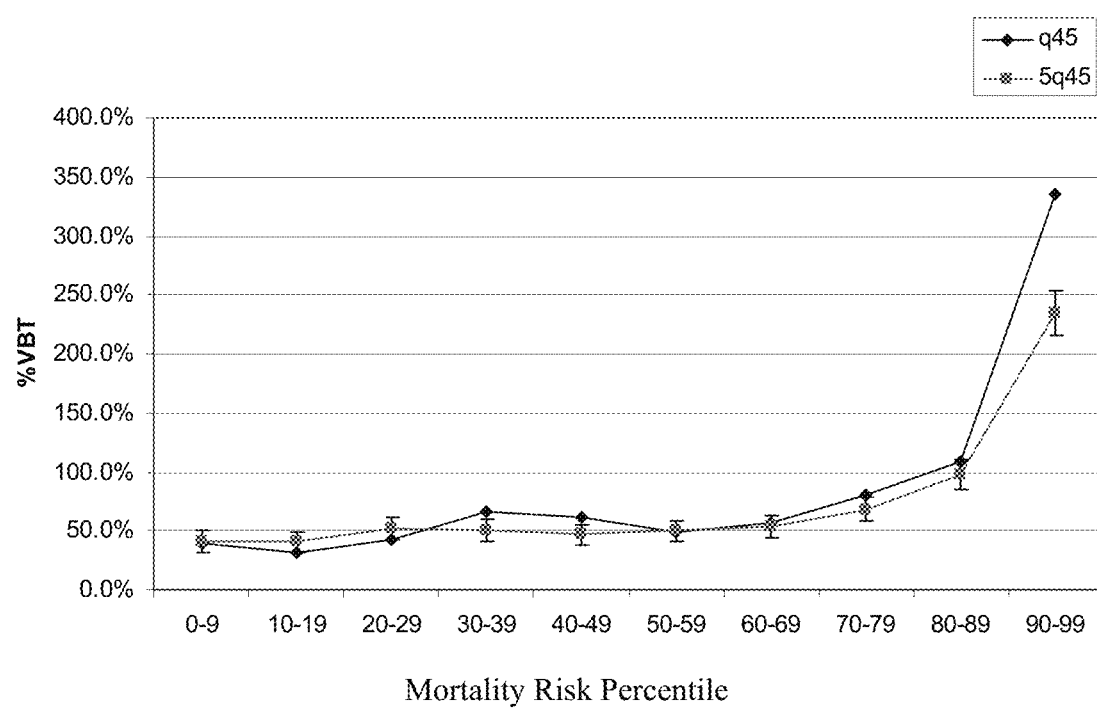
FIG. 7 shows a comparison of 7-year mortality rates of 5.95 million scorable individuals as a percentage of the 2001 Valuation Basic Table (VBT, published by the Society of Actuaries) according to Mortality Risk Percentile deciles. Details are discussed in Example 2.

As the Mortality Risk Assessment Model presented herein successfully excludes high-risk applicants from its lower ranges, it disproportionately concentrates them among higher scores. As seen in FIG. 7, above a Mortality Risk Percentile of about 75, the mortality risk increases in an approximately exponential fashion, such that the average individual placed in the highest (90-99) decile died at more than 250% of the 2001 VBT Select rate, while the most mortality-prone percentile (Risk IQ 99) experienced nearly a 10-fold multiple of the VBT.

Example 3: Underwriting Requirements and the Mortality Risk Assessment Model Given the extremely favorable mortality rates among scores of 74 and below (described in Example 2), it is reasonable to question the need for additional requirements in this group—particularly when the individual seeking an insurance policy offers of no indication of unusual medical conditions.

Table 5 illustrates that, although a majority of all reflex tests (the results of which are not reflected in the exemplary algorithms used in the methods herein) are ordered for applicants with low scores, in many cases half or more of all positive results originate among the ~25% of specimens with scores of 75 or more.

Microalbumin and CDT are particularly extreme cases of this trend: in 2009-2010, 61.6% of positive CDT, and nearly 75% of positive microalbumin results were attributable to the highest risk quartile. For PSA reflex tests, by contrast, positive results were distributed almost uniformly across the Mortality Risk Assessment percentile range, suggesting that a PSA reflex test may add significant predictive value.

TABLE 5

Reflex Orders and Positives in Risk IQ Scorable Applicants (2009-2010)

| Test | RIQ Range | <75 | 75+ |
| --- | --- | --- | --- |
| CDT | % Reflexes | 56.9% | 43.1% |
|  | % Positives | 38.4% | 61.6% |
| HAA | % Reflexes | 62.5% | 37.5% |
|  | % Positives | 51.9% | 48.1% |
| HEPC | % Reflexes | 75.0% | 25.0% |
|  | % Positives | 53.5% | 46.5% |
| A1C | % Reflexes | 75.3% | 24.7% |
|  | % Positives | 52.4% | 47.6% |
| PSA | % Reflexes | 82.2% | 17.8% |
|  | % Positives | 80.0% | 20.0% |
| UMALB | % Reflexes | 55.4% | 44.6% |
|  | % Positives | 25.2% | 74.8% |

Additionally, attending physician statements (APSs) are among the most costly and time consuming requirements likely to arise in the course of the life insurance application process. During 2009 and the first half of 2010, 80.3% of APS orders among scorable applicants were associated with scores of 74 and lower—individuals who could, based on laboratory results alone, be expected to experience preferred levels of mortality. Thus, a significant fraction of these requests could have been eliminated had the underwriter possessed evidence of low underlying risk.

Example 4: Comparison with Conventional Underwriting Criteria

While underwriting manuals naturally differ somewhat among carriers, prevailing underwriting standards are sufficiently similar that it is possible to consider a set of "generic preferred criteria". As applied to laboratory results in the course of this study, 35-40% of applicants met a fairly comprehensive set of guidelines for preferred criteria (among many others, $TC \leq 230$ or $TC \leq 250$ and $TC/HDL \leq 5$, systolic $BP < 140$, $20 < BMI < 28$). While there is clearly a strong relationship between underwriting status under existing conventional criteria and the Mortality Risk Assessment Model, the Mortality Risk Assessment Model diverges from the conventional criteria largely by accounting for the implications of an individual's profile as a whole, rather than as considering each variable individually (as done under conventional underwriting standards). For example, an applicant with multiple test results at the outer margins of the "normal" ranges may in fact represent an extremely elevated risk, while an applicant with a single "out-of-range" result, but an otherwise ideal profile, may well rank among the least risky of their peers.

Figure 8:
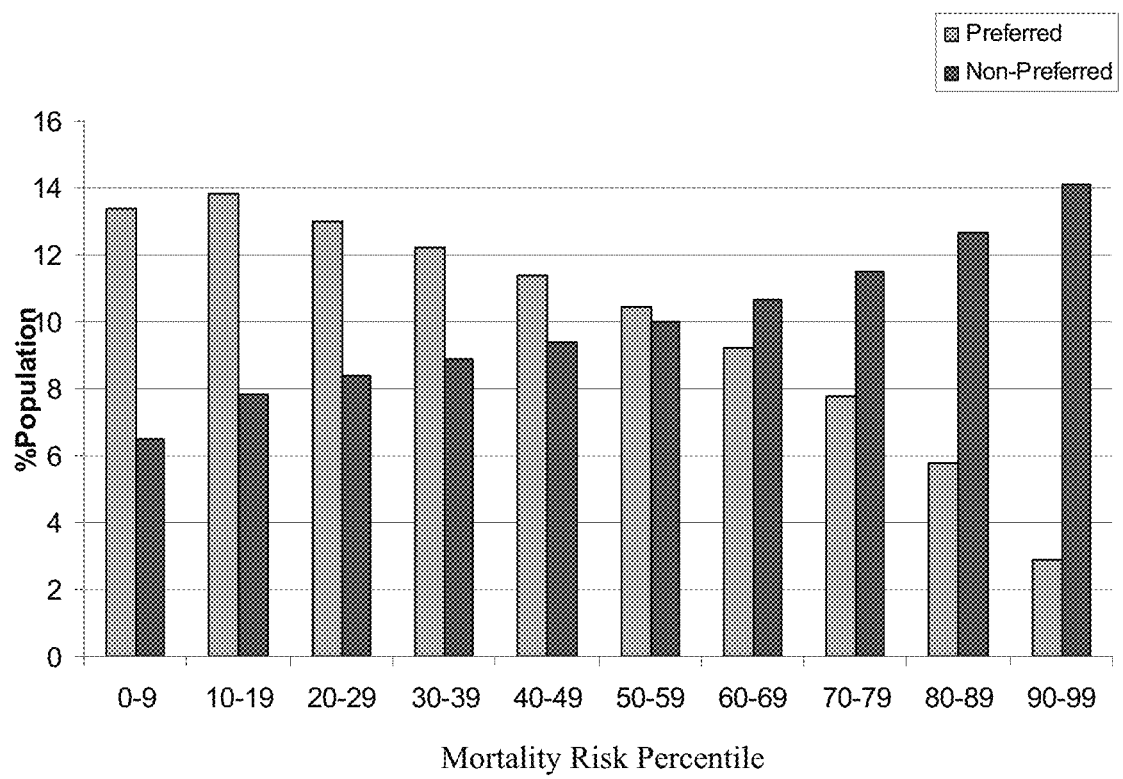
FIG. 8 shows a comparison of Generic Underwriting Class Distribution by Mortality Risk Percentile deciles. Details are discussed in Example 3.

FIG. 8 demonstrates the Generic Underwriting Class Distribution by Mortality Risk percentile. As assessed by the Mortality Risk Assessment Model, more than 30% of life insurance applicants currently excluded from preferred pools actually present lower mortality risks than the majority of preferred-qualified individuals. Conversely, more than 25% of preferred applicants actually exhibit higher mortality risk than most non-preferred individuals. Clear, identifiable deficiencies exist in traditional underwriting practices, resulting in the assignment of low-risk individuals to high-risk pools, and vice-versa.

Example 5: Cryptic Risk

A "cryptic risk" applicant is an individual who meets all conventional preferred criteria, yet whose profile generates a score of 75 or above as determined by methods presented herein. As discussed in Example 4, this most frequently results from the interaction of several "borderline normal" (in conventional terms) laboratory results, no one of which would necessarily appear worthy of attention in isolation. Among all applicants analyzed, 5.9% can be classified as cryptic risk. The lowest incidence is among females 60-79, at 3.2%; the highest is in males 18-29, at 8.9%.

Figure 9:
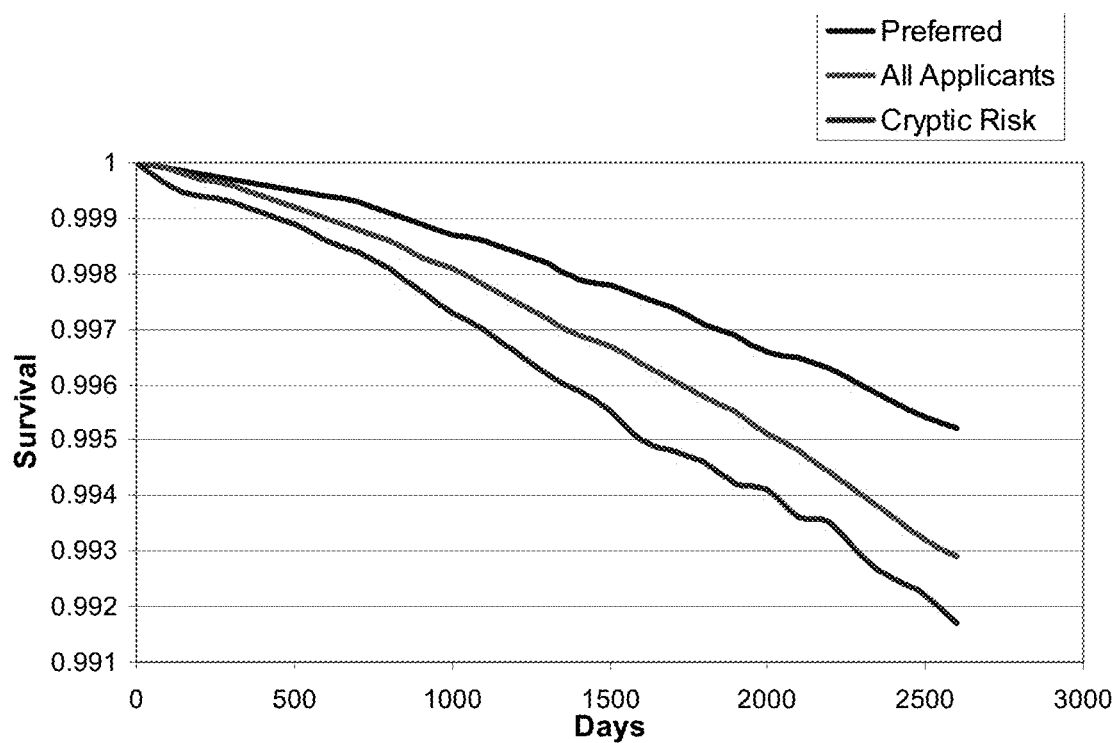
FIG. 9 shows cryptic risk and 7-year survival in 45-year old male non-tobacco users. Details are discussed in Example 4.

The typical cryptic risk applicant experiences a mortality risk of 142% VBT, more than twice the 63% observed of the preferred group as a whole in our data, as shown in FIG. 9. These individuals represent a significantly underpriced sub-population of life insurance applicants.

Example 6: Hidden Health

Conversely, a "hidden health" applicant is an individual who fails conventional preferred criteria, yet whose profile generates a score of less than 75 as determined by methods presented herein. These individuals represent a significantly over-priced sub-population. This group is substantially larger than the cryptic risk population (encompassing 30-40% of applicants, again varying somewhat by age and sex), although the discrepancy between actual and expected mortality is less extreme, on average, than in cryptic risk cases.

BMI is by a comfortable margin the most common grounds for the denial of preferred classification to the Hidden Healthy, followed more distantly by lipids (TC, TC/HDL, and LDL) and blood pressure (Table 6). The marketing implications of extending preferred rates to so large a population are substantial.

TABLE 8

Hidden Healthy Cause of Exclusion from Generic Preferred Pool in Males 40-49

| | |
| --- | --- |
| BMI | 72.9% |
| Lipids | 33.4% |
| Blood Pressure | 8.2% |

TABLE 8-continued

Hidden Healthy Cause of Exclusion from
Generic Preferred Pool in Males 40-49

| | |
|---|---|
| Urine Protein | 5.3% |
| Urine Hemoglobin | 3.3% |
| GGT | 2.4% |

Example 6: Hidden Health

A study was conducted comparing the results of the Mortality Risk Assessment Model with a fully underwritten policy population (Mortality Risk scored applicants=139,486, Deaths=716, Claims=307) are outlined below. As shown in Table 9, only a minority of all known deaths were reflected in claims (the remainder having presumably been declined, not taken out, or lapsed prior to death), The disproportionately low death/claims ratio in high-Mortality Risk percentile applicants strongly suggests an enhanced propensity to decline these individuals, even under conventional underwriting criteria—as would be expected given the correlation between the Mortality Risk Assessment Model and current underwriting criteria (demonstrated in FIG. 8). However, large numbers of high-scoring applications were fully underwritten, issued, and then fairly promptly paid as claims. Among the Mortality Risk 99$^{th}$ percentile alone (which reliably exhibit a 10-fold elevation of mortality rates) were ten paid claims totaling $2.5 million.

TABLE 9

Deaths and Claims in Fully Underwritten
Policies by Mortality Risk Percentile

| Mortality Risk Percentile | Deaths | Claims | % Deaths in Claims |
|---|---|---|---|
| 0-9 | 40 | 18 | 45.0% |
| 10-19 | 50 | 20 | 40.0% |
| 20-29 | 48 | 25 | 52.1% |
| 30-39 | 72 | 38 | 52.8% |
| 40-49 | 61 | 28 | 45.9% |
| 50-59 | 42 | 23 | 54.8% |
| 60-69 | 63 | 30 | 47.6% |
| 70-79 | 78 | 41 | 52.6% |
| 80-89 | 87 | 29 | 33.3% |
| 90-99 | 175 | 55 | 31.4% |
| 99 Only | 42 | 10 | 23.8% |
| Total | 716 | 307 | 42.9% |

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The methods illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof. It is recognized that various modifications are possible within the scope of the invention claimed. Thus, it should be understood that although the present invention has been specifically disclosed by preferred embodiments and optional features, modification and variation of the invention embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein.

What is claimed is:

1. A method of underwriting a life or medical insurance policy for an individual, the method comprising:
    measuring three or more laboratory analytes in a biological fluid sample of the individual using a bodily fluid analyzer, wherein the three or more laboratory analytes comprise three or more selected from the group consisting of Albumin (ALB), Alkaline Phosphatase (ALP), Alanine Aminotransferase (ALT), Aspartate Aminotransferase (AST), Bilirubin (BILI), Blood Urea Nitrogen (BUN), Cholesterol (CHOL), Urine Hydrochlorothiazide (Diuretic), Fructosamine (FRUC), Gamma-glutamyl Transferase (GGT), Blood sugar (GLUC), High Density Liporproteins (HDL), Total Protein (PROT), Triglycerides (TRIG), Urine Cotinine (UCOT), Urine Creatinine (UCREAT), Urine Glucose (UGLUC), Urine Hemosiderin (UHEMO), Urine Protein (UPROT), Urine pH (URNPH), Creatinine (CREAT), Urine Leukocyte Esterase (ULEUK), Urine Cocaine (UCOC), and Blood HIV (BLDHIV),
    determining, by a processor of a computer, a relative mortality risk of the individual based on a plurality of measurements of physical characteristics stored in a memory of the computer and on the three or more laboratory analytes of the individual measured using the bodily fluid analyzer, and
    determining, by the processor, a price for said life or medical insurance policy based on the relative mortality risk of the individual,
    wherein the method of determining, by the processor, the relative mortality risk of the individual comprises:
    (a) receiving the three or more laboratory analyte measurements from the bodily fluid analyzer;
    (b) assigning the individual to an age and gender group depending on the individual's age and gender;
    (c) adjusting at least one of the measurements for seasonal variances, taking the day of the year as an input, to produce an adjusted measurement;
    (d) creating a plurality of calculated measurements each of which takes two or more measurements as inputs and produces a calculated measurement as output;
    (e) generating an input variable for each adjusted measurement and calculated measurement, by (i) truncating a quantitative measurement between a pre-determined maximum level and a pre-determined minimum level and then generating a difference value between the truncated measurement and a pre-determined reference level, as an input variable, wherein the pre-determined maximum, minimum and reference levels are selected according to the individual's age and gender group, and (ii) converting a qualitative measurement to a positive/negative type input variable, a cutoff-based input variable or a comparison-based input variable as an input variable;

(f) calculating a relative mortality risk score using a multivariate model with predetermined coefficients and taking the input variables generated at step (e) as inputs; and (g) determining the relative mortality risk of the individual from the relative mortality risk score, which determination further takes into consideration tobacco use of the individual, wherein determining the relative mortality risk comprises (i) comparing the relative mortality risk score to a threshold, (ii) determining, if the relative mortality risk score is at or above the threshold but the individual meets conventional preferred criteria, that the individual is a cryptic risk applicant who has a relative mortality risk that is higher than a conventional mortality risk based on the conventional preferred criteria, and (iii) determining, if the relative mortality risk is below the threshold but the individual fails conventional preferred criteria, the individual is a hidden health individual who has a relative mortality risk that is lower than a conventional mortality risk based on the conventional preferred criteria.

2. The method of claim 1, wherein the relative mortality risk score is determined as $$HAZARD\_SCORE = HAZARD/ADJ\_FACTOR*100,$$

wherein $$HAZARD = e^{\hat{}\Sigma_{n=1}^{-122} \beta_n VAR_n},$$

$\beta_n$ denotes a predetermined coefficient,
$VAR_n$ denotes an input variable, and
ADJ_FACTOR is a reference risk factor specific to a corresponding individual group.

3. The method of claim 1, wherein said multivariate model is a Cox proportional hazards multivariate regression model.

4. The method of claim 1, wherein said predetermined coefficients are determined using physical characteristics and analyte levels from a plurality of individuals.

5. The method of claim 1, wherein said analytes comprise at least four selected from the group.

6. The method of claim 1, wherein said physical characteristics comprise at least three.

7. The method of claim 1, wherein the reference level is the median level.

8. The method of claim 1, wherein said physical characteristics are selected from the group consisting of height, weight, diastolic blood pressure, systolic blood pressure, pulse, and body mass index.

9. The method of claim 1, wherein said physical characteristics comprise height, weight, diastolic blood pressure, systolic blood pressure, pulse, and body mass index.

10. The method of claim 1, wherein said relative mortality risk is scaled to 100.

11. The method of claim 1, further comprising outputting the relative mortality risk to a non-transitory computer readable media.

12. The method of claim 1, further comprising acquiring the biological fluid sample from the individual and delivering the biological fluid sample to the bodily fluid analyzer, wherein the biological fluid sample includes at least one of blood, plasma, serum, and urine of the individual.

13. The method of claim 1, further comprising measuring the plurality of physical characteristics of the individual and saving the plurality of physical characteristics in the memory of the computer.

14. A computing system for underwriting a life or medical insurance policy, the system comprising a bodily fluid analyzer, a processor, and a memory having instructions that, when executed by the processor, cause the computing system to:

measure three or more laboratory analytes in a biological fluid sample of an individual using the bodily fluid analyzer, wherein the three or more laboratory analytes comprise three or more selected from the group consisting of Albumin (ALB), Alkaline Phosphatase (ALP), Alanine Aminotransferase (ALT), Aspartate Aminotransferase (AST), Bilirubin (BILI), Blood Urea Nitrogen (BUN), Cholesterol (CHOL), Urine Hydrochlorothiazide (Diuretic), Fructosamine (FRUC), Gamma-glutamyl Transferase (GGT), Blood sugar (GLUC), High Density Liporproteins (HDL), Total Protein (PROT), Triglycerides (TRIG), Urine Cotinine (UCOT), Urine Creatinine (UCREAT), Urine Glucose (UGLUC), Urine Hemosiderin (UHEMO), Urine Protein (UPROT), Urine pH (URNPH), Creatinine (CREAT), Urine Leukocyte Esterase (ULEUK), Urine Cocaine (UCOC), and Blood HIV (BLDHIV);

determine the relative mortality risk of the individual based on a plurality of measurements of physical characteristics of the individual stored in the memory and on the laboratory analytes measured using the bodily fluid analyzer; and determine a price for said life or medical insurance policy based on the determined relative mortality risk of the individual;

wherein determining the relative mortality risk of the individual comprises:

(a) assigning the individual to an age and gender group depending on the individual's age and gender;

(b) adjusting at least one of the laboratory analyte and physical characteristic measurements for seasonal variances, taking the day of the year as an input, to produce an adjusted measurement;

(c) creating a plurality of calculated measurements each of which takes two or more measurements as inputs and produces a calculated measurement as output;

(d) generating an input variable for each adjusted measurement and calculated measurement, by (i) truncating a quantitative measurement between a pre-determined maximum level and a pre-determined minimum level and then generating a difference value between the truncated measurement and a pre-determined reference level, as an input variable, wherein the pre-determined maximum, minimum and reference levels are selected according to the individual's age and gender group, and (ii) converting a qualitative measurement to a positive/negative type input variable, a cutoff-based input variable or a comparison-based input variable as an input variable;

(e) calculating a relative mortality risk score using a multivariate model with predetermined coefficients and taking the input variables generated at step (d) as inputs; and (f) determining the relative mortality risk of the individual from the relative mortality risk score, which determination further takes into consideration tobacco use of the individual, wherein determining the relative mortality risk comprises (i) comparing the relative mortality risk score to a threshold, (ii) determining, if the relative mortality risk score is at or above the threshold but the individual meets conventional preferred criteria, that the individual is a cryptic risk applicant who has a relative mortality risk that is higher than a conventional mortality risk based on the conventional preferred criteria, and (iii) determining, if the relative mortality risk is below the threshold but the individual fails conventional preferred criteria, the individual is a hidden health individual who has a relative mortality risk that is lower than a conventional mortality risk based on the conventional preferred criteria.

* * * * *